(12) United States Patent
Maxwell et al.

(10) Patent No.: US 11,026,706 B1
(45) Date of Patent: Jun. 8, 2021

(54) MODULATION OF TRANSDUCER AMPLITUDE AND PHASE DISTRIBUTIONS FOR CONTROLLED APPLICATION OF RADIATION FORCE TO AN OBJECT

(71) Applicants: University of Washington, Seattle, WA (US); SonoMotion Inc., South San Francisco, CA (US)

(72) Inventors: Adam D. Maxwell, Seattle, WA (US); Doug Corl, Seattle, WA (US)

(73) Assignees: University of Washington, Seattle, WA (US); SonoMotion Inc., South San Francisco, CA (US)

( * ) Notice: Subject to any disclaimer, the term of this patent is extended or adjusted under 35 U.S.C. 154(b) by 556 days.

(21) Appl. No.: 15/818,626

(22) Filed: Nov. 20, 2017

Related U.S. Application Data

(60) Provisional application No. 62/423,866, filed on Nov. 18, 2016.

(51) Int. Cl.
| | | |
|---|---|---|
| A61B 17/22 | (2006.01) |
| A61B 8/08 | (2006.01) |
| A61B 8/00 | (2006.01) |
| A61B 17/225 | (2006.01) |

(52) U.S. Cl.
CPC ........ *A61B 17/22004* (2013.01); *A61B 8/085* (2013.01); *A61B 8/4494* (2013.01); *A61B 17/225* (2013.01); *A61B 17/2258* (2013.01); *A61B 2017/22028* (2013.01)

(58) Field of Classification Search
CPC ............ A61B 17/22004; A61B 17/225; A61B 17/2258; A61B 8/085; A61B 8/4494; A61B 2017/22028
See application file for complete search history.

(56) References Cited

U.S. PATENT DOCUMENTS

| | | |
|---|---|---|
| 6,540,700 B1 | 4/2003 | Fujimoto et al. |
| 7,344,509 B2 | 3/2008 | Hynynen et al. |
| 2008/0045864 A1 | 2/2008 | Candy et al. |
| 2011/0263967 A1 | 10/2011 | Bailey et al. |

FOREIGN PATENT DOCUMENTS

WO 2016/061587 A1 4/2016

OTHER PUBLICATIONS

Bailey, M., et al., "Ultrasonic Propulsion of Kidney Stones: Preliminary Results of a Human Feasibility Study," Proceedings of the IEEE International Ultrasonics Symposium, Sep. 3-6, 2014, Chicago, pp. 511-514.

(Continued)

*Primary Examiner* — Michael T Rozanski
(74) *Attorney, Agent, or Firm* — Christensen O'Connor Johnson Kindness PLLC

(57) ABSTRACT

Disclosed herein are ultrasound systems comprising a plurality of transducers configured to work in concert to produce a customizable beam profile through the additive effects of multiple pulses. As an example, uniform and wide beam profiles can be generated using transducer elements that cannot independently generate such beam profiles. Related methods, systems, and computer-readable media are all disclosed.

20 Claims, 22 Drawing Sheets
(18 of 22 Drawing Sheet(s) Filed in Color)

(56) References Cited

OTHER PUBLICATIONS

Connors, B.A., et al., "Comparison of Tissue Injury From Focused Ultrasonic Propulsion of Kidney Stones Versus Extracorporeal Shock Wave Lithotripsy," Journal of Urology 191(1):235-241, Jan. 2014.

Harper, J.D., et al., "First in Human Clinical Trial of Ultrasonic Propulsion of Kidney Stones," Journal of Urology 195(4, Part 1):956-964, Apr. 2016.

Harper, J.D., et al., "Preclinical Safety and Effectiveness Studies of Ultrasonic Propulsion of Kidney Stones," Urology 84(2):484-489, Aug. 2014.

Hyams, E.S., and B.R. Matlaga, "Economic Impact of Urinary Stones," Translational Andrology and Urology 3(3):278-283, Sep. 2014.

Maxwell, A.D., et al., "Fragmentation of Urinary Calculi In Vitro by Burst Wave Lithotripsy," Journal of Urology 193(1):338-344, Jan. 2015.

May, P.C., et al., "Ultrasonic Propulsion of Kidney Stones," Current Opinion in Urology 26(3):264-270, May 2016.

Scales, C.D., et al., "Prevalence of Kidney Stones in the United States," European Urology 62(1):160-165, Jul. 2012.

Shah, A., et al., "Novel Ultrasound Method to Reposition Kidney Stones," Urological Research 38(6):491-495, Dec. 2010.

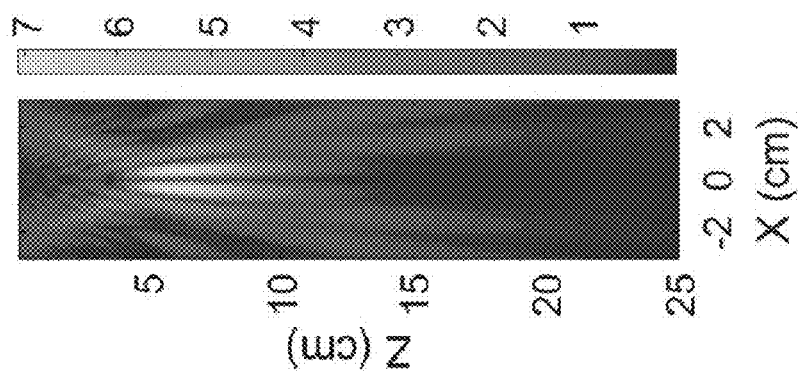
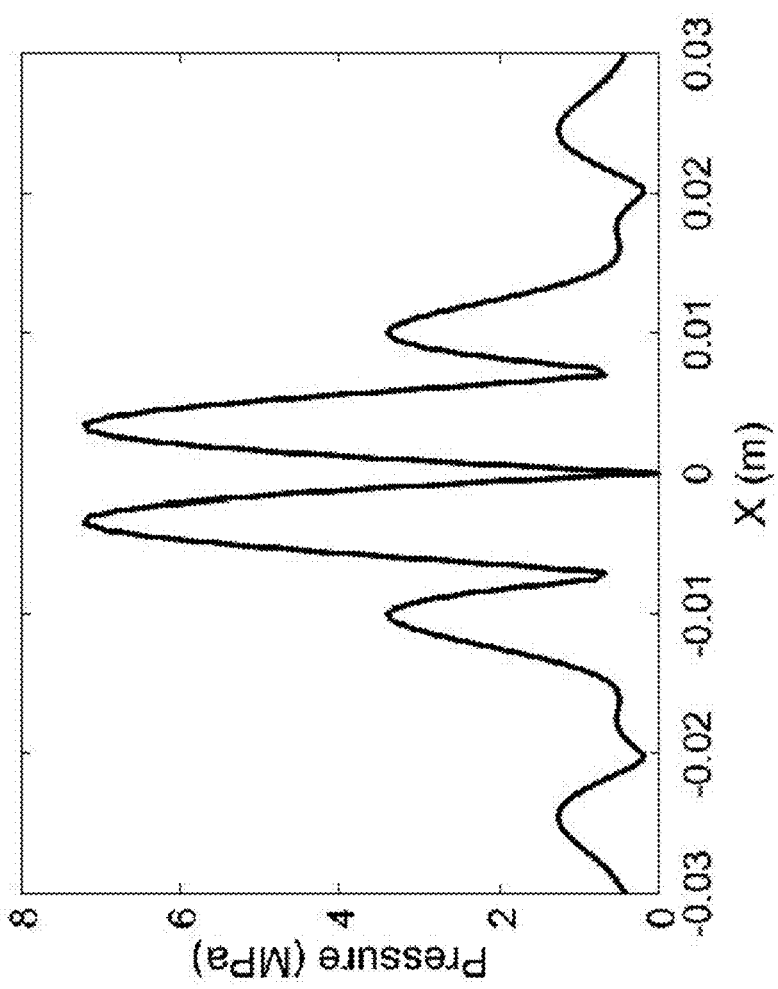
FIG. 1B

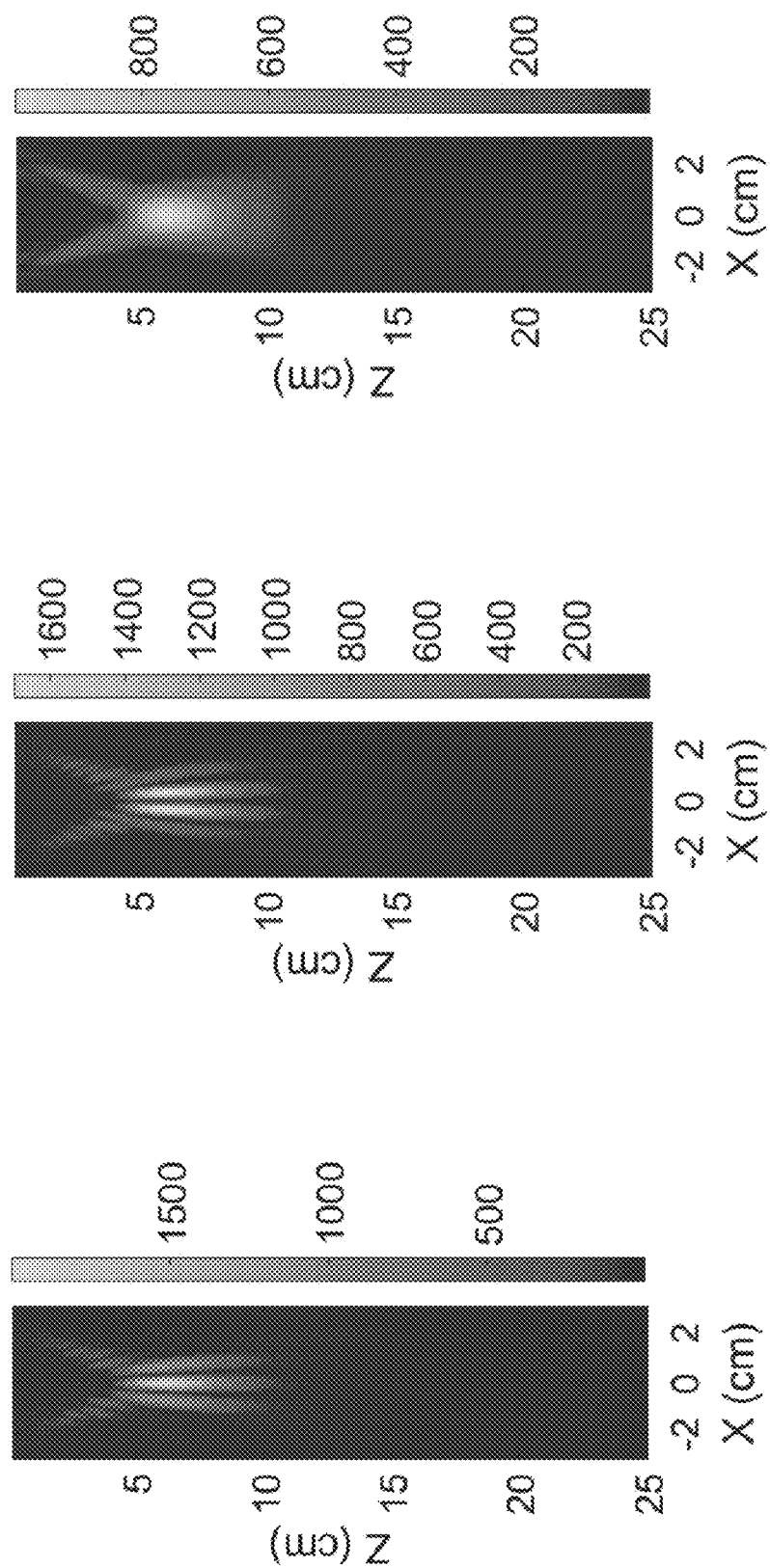

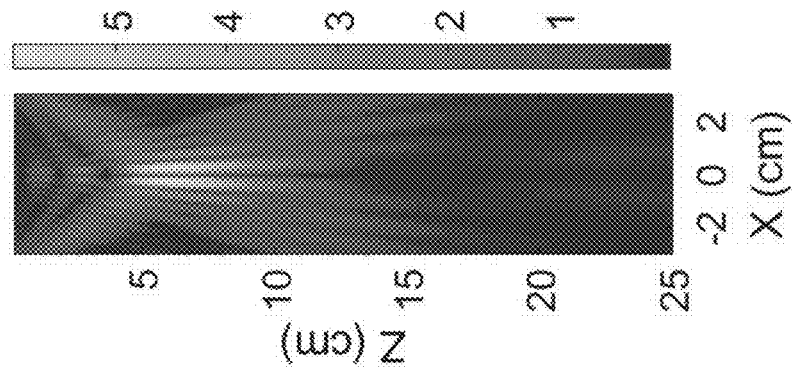
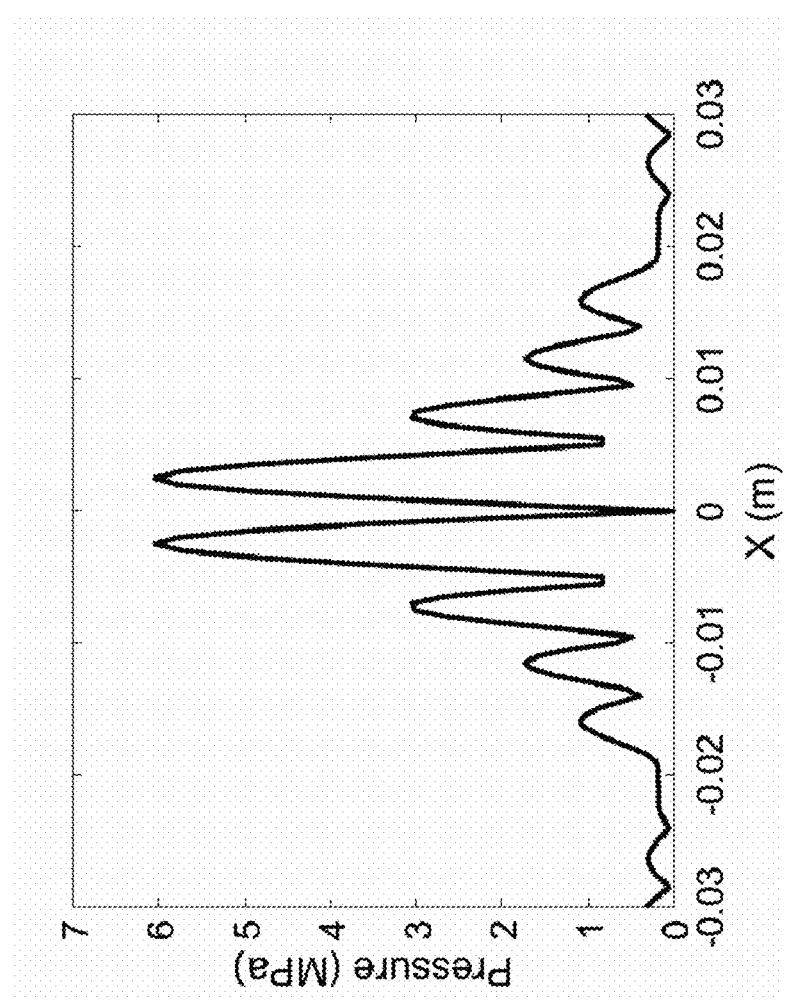
FIG. 5B

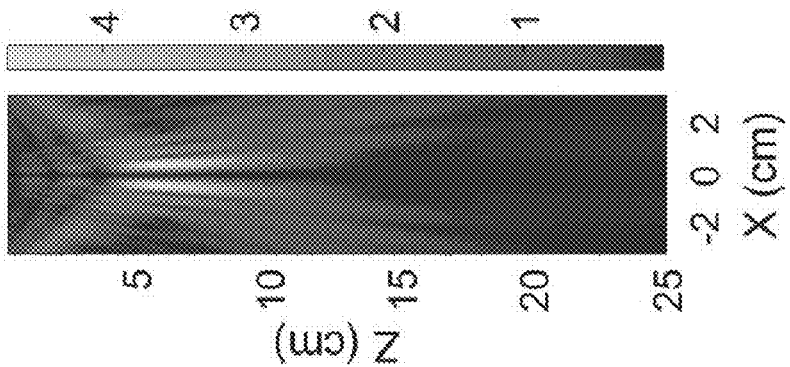
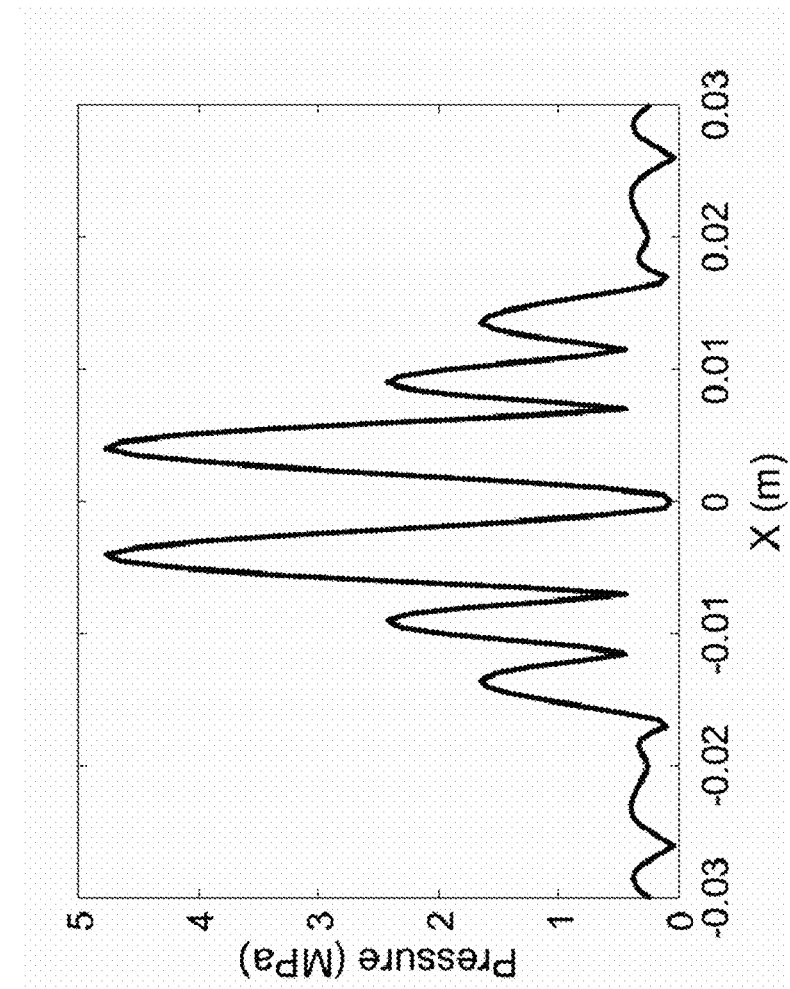
FIG. 5C

MODULATION OF TRANSDUCER AMPLITUDE AND PHASE DISTRIBUTIONS FOR CONTROLLED APPLICATION OF RADIATION FORCE TO AN OBJECT

CROSS-REFERENCE TO RELATED APPLICATION

This application claims the benefit of U.S. Provisional Application No. 62/423,866, filed Nov. 18, 2016, the disclosure of which is expressly incorporated herein by reference in its entirety.

STATEMENT OF GOVERNMENT LICENSE RIGHTS

This invention was made with government support under Grant No. K01 DK104854, awarded by the National Institutes of Health. The government has certain rights in the invention.

BACKGROUND

This application relates to ultrasound imaging and therapies—specifically those involving radiation force. Radiation force may be generated by ultrasound to apply translational momentum to an object or part of an object. This effect can be used for diagnostic or imaging purposes. For instance, in imaging, one may apply an ultrasound pulse to generate a transient radiation force on a tissue. By observing the resulting displacement and rebound of the tissue, one can estimate the stiffness of the tissue. Ultrasound may also be used to noninvasively move objects in the body, such as kidney stones, for the purpose of encouraging passage of stones through the urinary tract. This application is known as ultrasonic propulsion (UP).

In UP, ultrasound is usually applied as a focused beam. The beam may be focused by either a geometrically focused transducer or by proper phasing techniques using a phased array. In most cases, it is desirable to achieve a relatively uniform beam, such that the operator can easily anticipate the movement of stones prior to applying a "push." Another desirable feature in some cases is to have a wide beamwidth that can push many stone fragments in a short time. While such characteristics can be achieved with a small transducer of simple geometry, it is additionally desirable to incorporate an imaging transducer for treatment guidance. The insertion of an imaging probe complicates the geometry of the UP transducer, particularly when the imager and UP transducer are of similar surface area, thus producing a complex and distorted beam field. Furthermore the transducer cannot be so small that it is incapable of producing sufficient acoustic power. Thus, it is a challenge to produce a wide, uniform intensity beam of sufficient power in the case of a small (i.e. with dimensions comparable to an ultrasound imaging probe), image-guided UP transducer.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect a method for applying ultrasound energy to an object disposed in a patient is provided. In one embodiment the method includes applying ultrasound energy to the object using a segmented therapy transducer having a plurality of elements excited by a plurality of phasing profiles; wherein the plurality of phasing profiles exciting the plurality of elements collectively generates an ultrasound beam having a time-averaged intensity profile that is generated over a larger area or more uniform than a comparative time-averaged intensity profile generated by the plurality of elements but without the plurality of phasing profiles. In another aspect a system for applying an ultrasound force to an object disposed in a patient is provided. In one embodiment, the system includes:

a multi-element transducer having a first element and a second element, wherein the multi-element transducer is configured and arranged to perform any of the methods disclosed herein.

In yet another aspect, provided is a non-transitory computer readable medium having computer executable instructions stored thereon that, if executed by one or more processors of a computing device, cause the computing device to perform any of the methods disclosed herein.

DESCRIPTION OF THE DRAWINGS

The patent or application file contains at least one drawing executed in color. Copies of this patent or patent application publication with color drawings will be provided by the Office upon request and payment of the necessary fee.

The foregoing aspects and many of the attendant advantages of this invention will become more readily appreciated as the same become better understood by reference to the following detailed description, when taken in conjunction with the accompanying drawings, wherein:

FIGS. 1A and 1B. Pressure profiles for a transducer made with two confocal elements, applying in phase (FIG. 1A) and 180-degree out-of-phase (FIG. 1B) excitation.

FIGS. 2A-2C. The summation (FIG. 2C) of the time-averaged intensity field distributions of the in-phase (FIG. 2A) and out-of-phase (FIG. 2B) fields from FIGS. 1A and 1B.

FIG. 4A is a projection of transducer layout and phasing to achieve vortex beams. A uniform phase distribution (m=0) is applied to the elements of an annular transducer, producing a focused beam in FIG. 4B. A transducer profile with an m=1 vortex phasing is shown in FIG. 4C. In practice, the transducer phasing may be separated into sectors that are driven with phase shifts corresponding to their circumferential position. The color scales on FIGS. 4B and 4C are angular phase—with FIG. 4B illustrating constant angular phase.

FIGS. 5A-5C. x-axis beam plot (left) and field intensity plots (right) for the transducer in FIGS. 4A-4C, phased for topological charges of m=0, 1, 2 for FIGS. 5A-5C, respectively.

FIGS. 8B and 8C are illustrations of an exemplary device comprising a single phased-array imaging probe situated at the center of eight therapy elements, wherein FIG. 8B is a perspective view and FIG. 8C is a longitudinal cross-sectional view.

DETAILED DESCRIPTION

Figure 1A:
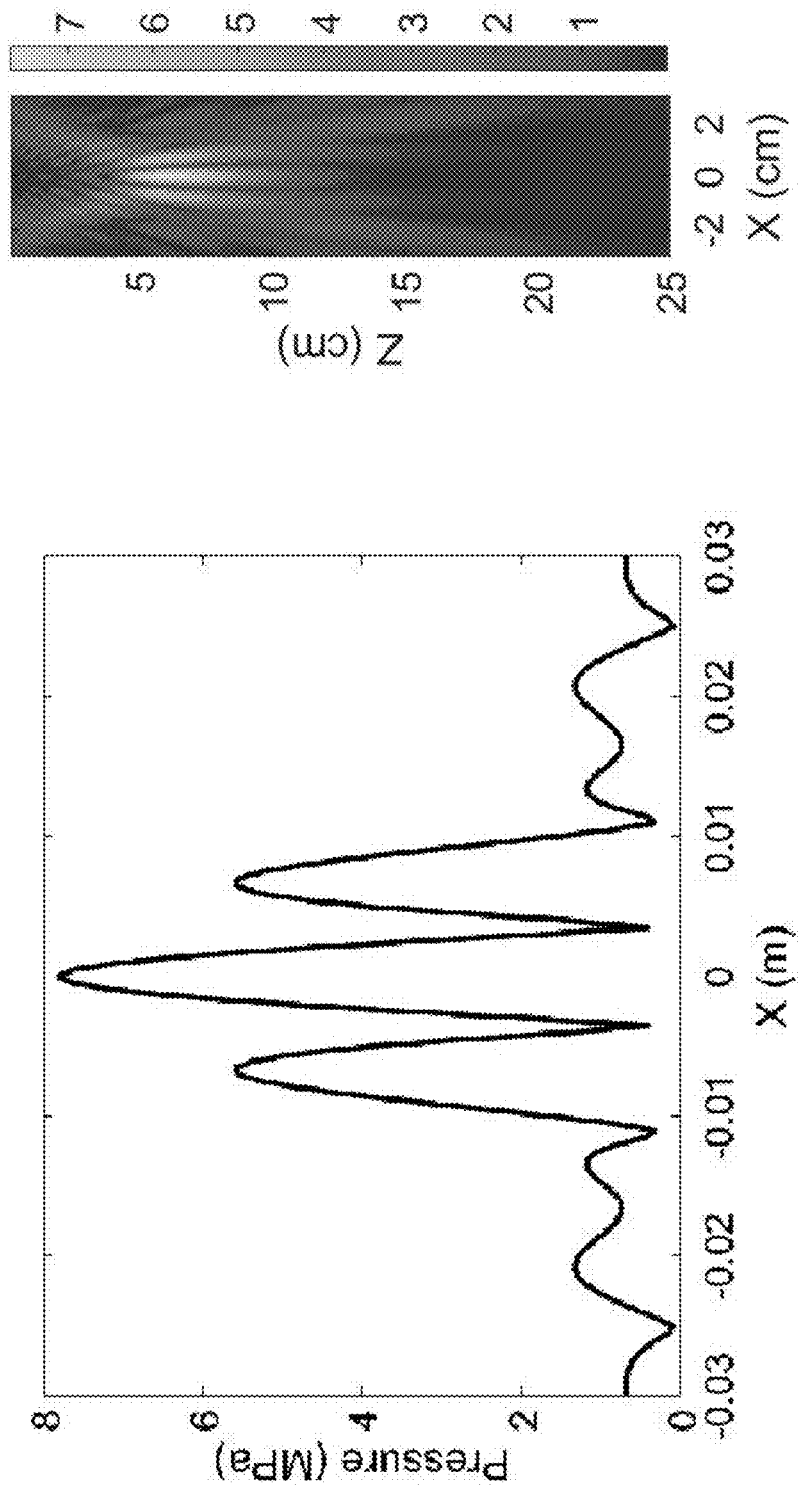

The present disclosure relates to ultrasound systems comprising a plurality of transducers configured to work in concert to produce a customizable beam profile through the additive effects of multiple pulses. As an example, uniform and wide beam profiles can be generated using transducer elements that cannot independently generate such beam profiles. Related methods, systems, and computer-readable media are all disclosed. In particular, using multiple amplitude and phasing profiles delivered in rapid succession or alternation to produce a desired time-averaged intensity profile, whereby radiation force is proportional to the intensity at a given point.

The present disclosure improves upon, incorporates, and/or is related to one or more of the inventors' previous U.S. patents and U.S. patent application publications, including: U.S. Pat. Nos. 7,033,328, 7,267,654, 8,535,250, 9,204,859, 9,597,102, 9,597,103, 9,597,103, and 9,743,909; and U.S. Patent Application Publication Numbers 2014/0081174, 2016/028790, 2017/0072225, US 2017/0245874, 2017/0249932, and 2017/0273699. The disclosures of these patents and published applications are hereby incorporated by reference in their entirety.

Definitions

The term "therapy exposure" relates herein to a series of pulses over an exposure time. The exposure time is defined in certain embodiments by a user activating the therapy probe by an on switch or other mechanism. An exemplary mechanism is on on/off switch, such as a foot-activated switch. Several therapy exposures may be utilized by a user during treatment of a patient for a cumulative therapy exposure session. Therapy exposures end when the system is continuously off for a prolonged period (e.g., 1 second or greater). An "off" period between pulses (i.e., when the duty cycle is less than 100%) does not mark the end of a therapy exposure.

It should be noted that while the disclosed embodiments are described in the context of moving kidney stones (or fragments thereof) using broadly focused ultrasound, the concepts disclosed herein can also be used to move other embedded objects, including, but not limited to, stones, fragments, blood clots, bullets, mucous, cystic fibrosis mucous, flowing blood, impacted stool in constipation, rectal, urethral and bladder foreign bodies, ureteral stones, bladder stones, airway foreign bodies, nasal congestion, sinus obstruction, impacted cerumen (ear wax), tissue flaps (like a torn retina), or floating objects in the eye and dust located in any of the gall bladder, the salivary tract, biliary tract or any other anatomical location of a human or other mammal. An additional use for the disclosed embodiments is to become a part of the maintenance program of implanted foreign bodies to prevent encrustation or occlusion over time. For example, ureteral stents become encrusted from urine solutes precipitating over time on the surface of the stent. The stent could receive intermittent pushing every 3 weeks to "disrupt" or slow the encrustation process. A similar embodiment could be envisioned for cardiac stents.

Stone or object: any piece of calculus material such as may be found, for example, in an organ, duct or vessel of a mammal, and including stones, stone fragments, and stone dust that may result from the application of shock waves or other therapeutic procedures; and equivalent embedded objects for which movement or displacement is desired. In one embodiment, the object is selected from the group consisting of a kidney stone, fragments, blood clots, bullets, mucous, cystic fibrosis mucous, flowing blood, impacted stool in constipation, rectal, urethral and bladder foreign bodies, ureteral stones, bladder stones, airway foreign bodies, nasal congestion, a sinus obstruction, impacted cerumen (ear wax), tissue flaps, floating objects in the eye, and dust located in the gall bladder, the salivary tract, the biliary tract, or any other anatomical location of a human or other mammal. In a further embodiment the object is, particularly, a kidney stone.

Pressure amplitude: the maximum deviation of the acoustic pressure from ambient.

Duty cycle (also referred to as duty factor): the fraction or percentage of time that the therapy transducers are activated during a single exposure, calculated as pulse duration multiplied by pulse repetition frequency. Duty cycle is typically expressed as a percentage.

Power: Energy per time, for both electric and acoustic power. Electric power excites the transducer element as a source; acoustic power is in the acoustic wave generated by the transducer element.

Intensity: power transmitted through a unit cross-sectional area.

Figure 11:
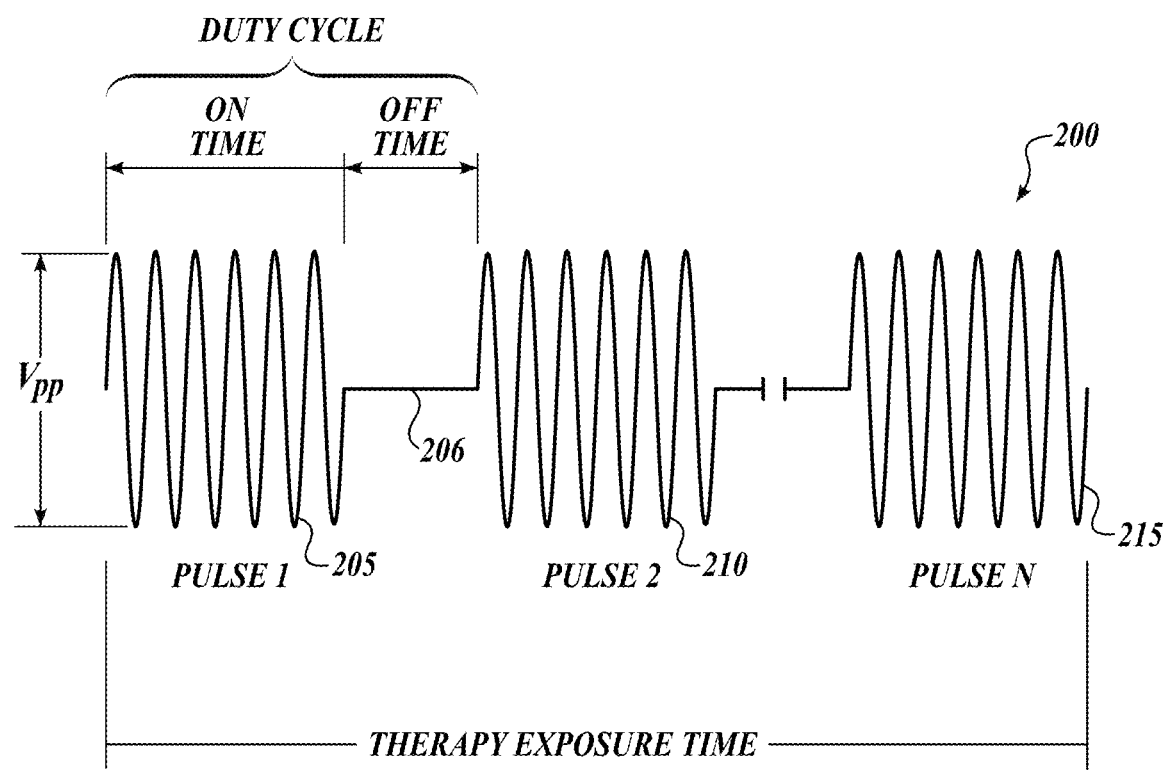
FIG. 11 illustrates an exemplary ultrasonic therapy exposure in accordance with embodiments disclosed herein.

Pulse: an acoustic wave of a certain duration. A single pulse encompasses one or several cycles of pressure oscillation at the center frequency. The excitation of one or more elements in the transducer generates a pulse. Pulses in B-mode ultrasound imaging tend to be 1-2 cycles. The pulse created by a shock wave lithotripter tends to be 1 cycle. The pulses used for UP tend to be in the range from 100 to 50,000 cycles, more commonly in the range from 3000 to 15,000 cycles. The pulses for BWL or breakwave lithotripsy are typically in the range of 10 to 100 cycles. FIG. 11 illustrates a therapy exposure 200 comprising a number of pulses 205, 210, 215. Each pulse 205 et al. has an "on" time which is followed by an "off" time 206 in which the imaging probe can operate to produce at least two frames per second. This frame rate, while low, still allows an operator to track kidney stones exposed to the therapy exposure sufficiently.

B-mode ultrasound: a mode of ultrasound used to create an image of anatomical structures.

Ultrasound waves can be characterized by any one or more of the following intensity parameters:

Temporal peak, $I_{TP}$, is the highest instantaneous intensity in the beam.

Temporal average, $I_{TA}$, is the time averaged intensity over the pulse repetition period (or other relevant time window).

Pulse average, $I_{PA}$, is the average intensity of the pulse.

Spatial peak, $I_{SP}$, is the highest intensity spatially in the beam.

Spatial average, $I_{SA}$, is the average intensity over a selected area.

Spatial average-temporal average intensity, $I_{SATA}$, is the acoustic power contained in the beam in watts averaged over at least one pulse repetition period, and divided by the area of interest.

Spatial average-pulse average intensity, $I_{SAPA}=I_{SATA}$/duty cycle, since $I_{PA}=I_{TA}$/duty cycle.

Spatial peak-temporal average intensity, $I_{SPTA}=I_{SATA}(I_{SP}/I_{SA})$.

Spatial peak-pulse average intensity, $I_{SPPA}=I_{SPTA}$ times duty cycle.

As used herein, the term "about" indicates that the subject value can be modified by plus or minus 5% and still fall within the disclosed embodiment.

Methods of Applying Ultrasound Energy

In one aspect a method for applying ultrasound energy to an object disposed in a patient is provided. In one embodiment the method includes applying ultrasound energy to the object using a segmented therapy transducer having a plurality of elements excited by a plurality of phasing profiles; wherein the plurality of phasing profiles exciting the plurality of elements collectively generates an ultrasound beam having a time-averaged intensity profile that is generated over a larger area or more uniform than a comparative time-averaged intensity profile generated by the plurality of elements but without the plurality of phasing profiles.

With regard to the time-averaged intensity profile this can be referred to as $I_{TA}$, time-averaged intensity (over the appropriate time window). It can be averaged over just a single pulse, if the pulse is partially in-phase, and partially out-of-phase as described later. In more complex schemes, there might be one pulse as a centrally focused beam, one pulse first order vortex, and one pulse second order vortex, in which case the appropriate time average would encompass at least three successive pulses. The intensity here is a continuous function of position (known as a field), not a spatially-averaged or spatial-peak value. $I_{TA}$ is a field, while $I_{SPTA}$ and $I_{SATA}$ are single values.

Figure 7A:
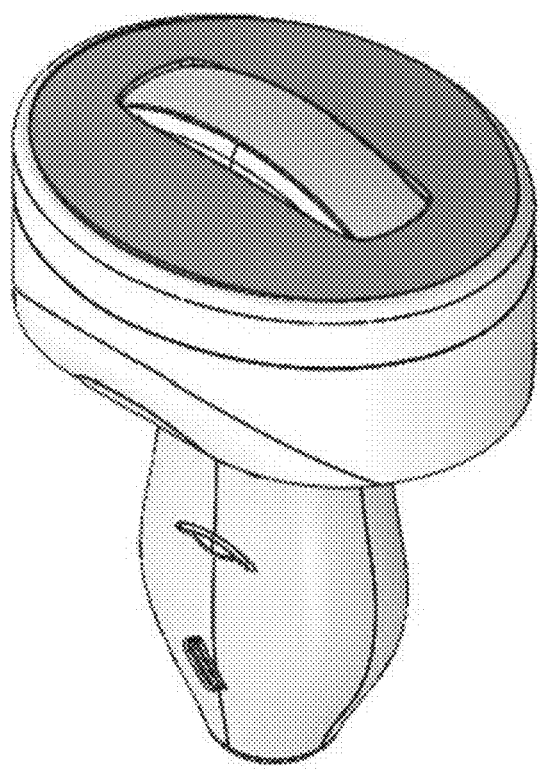
FIGS. 7A-7F are illustrations of an exemplary device comprising a single phased-array imaging probe situated between two therapy elements.
Figure 7B:
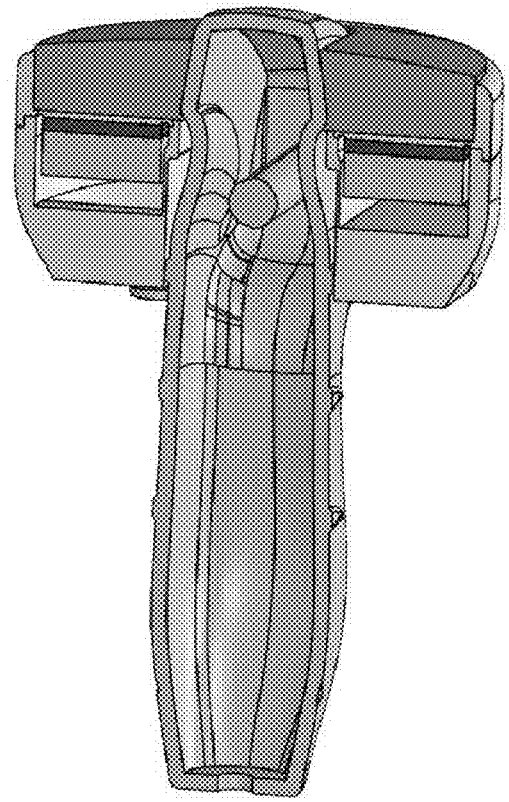
Figure 7C:
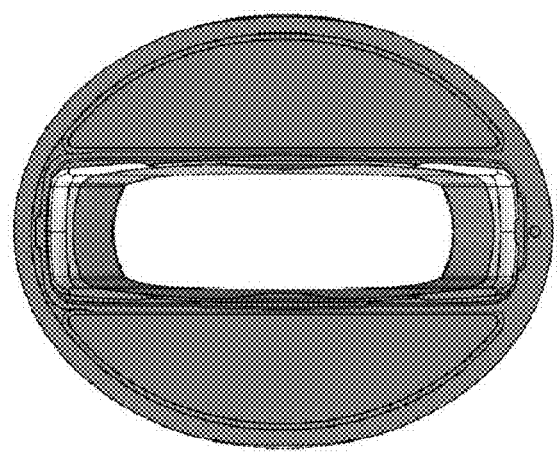
Figure 7D:
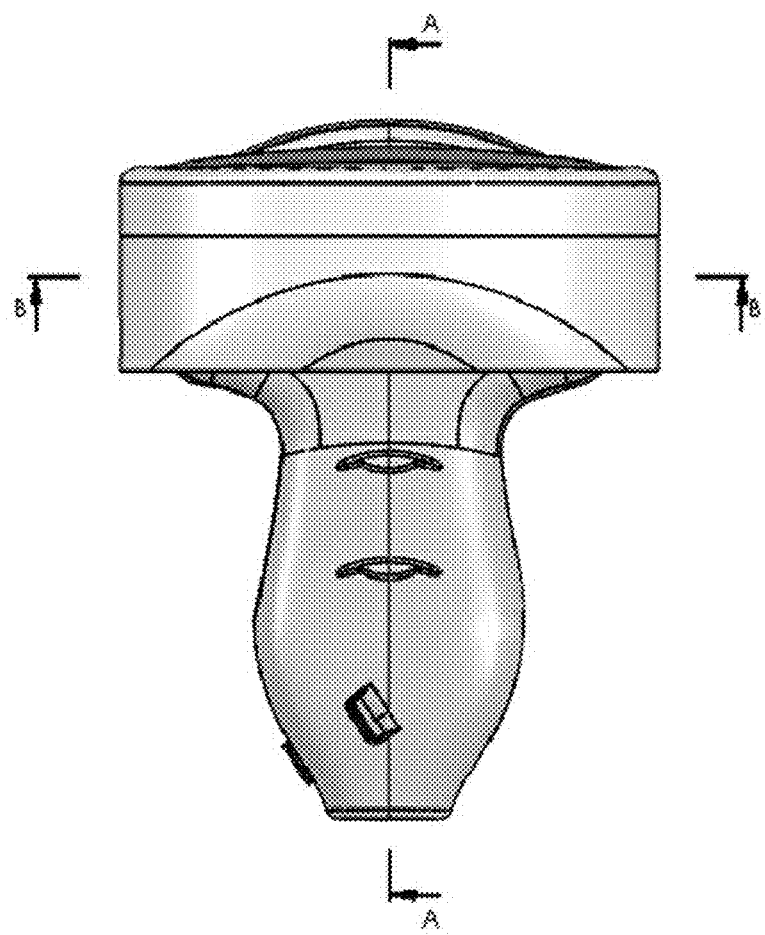
Figure 7E:
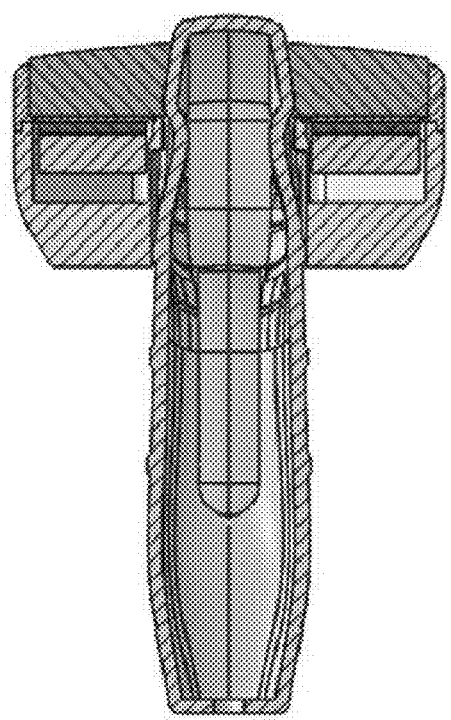
Figure 7F:
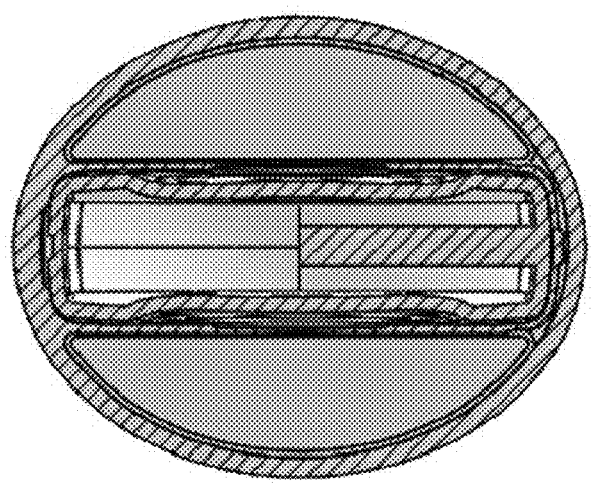

In the simplest form, a two-element therapy transducer is constructed as two identical elements offset along a specific dimension, such as the transducer illustrated in the probe of FIGS. 7A-7F (the two therapy transducers can be seen clearly in FIG. 7E). Such a configuration may be useful to insert an imaging probe inline (e.g., the central rectangular imaging transducer that is the topmost feature at the center of the probe of FIG. 7A).

Figure 8A:
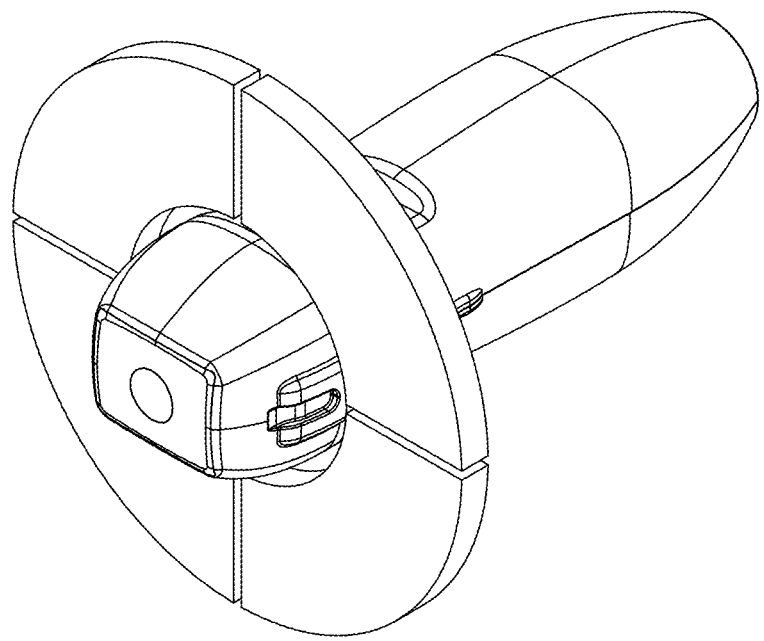
FIG. 8A is an illustration of an exemplary device comprising a single phased-array imaging probe situated at the center of four therapy elements.
Figure 8B:
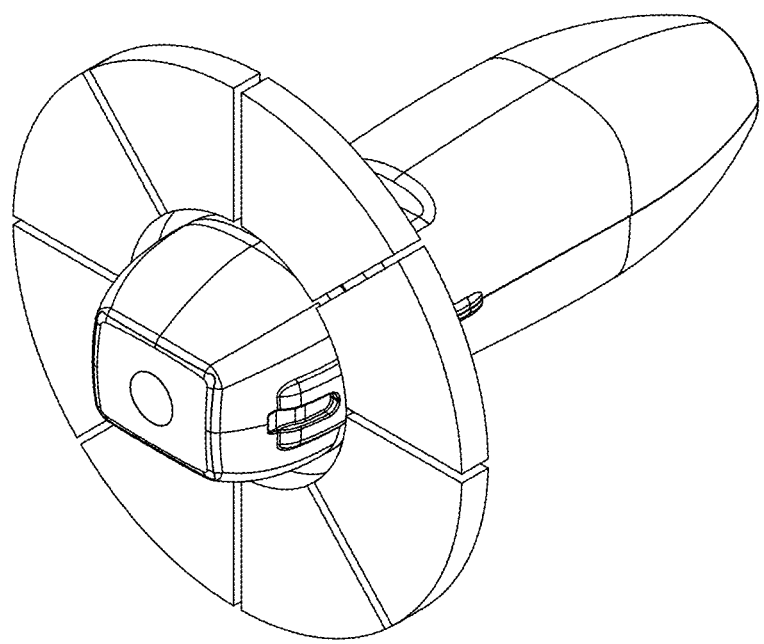
Figure 8C:
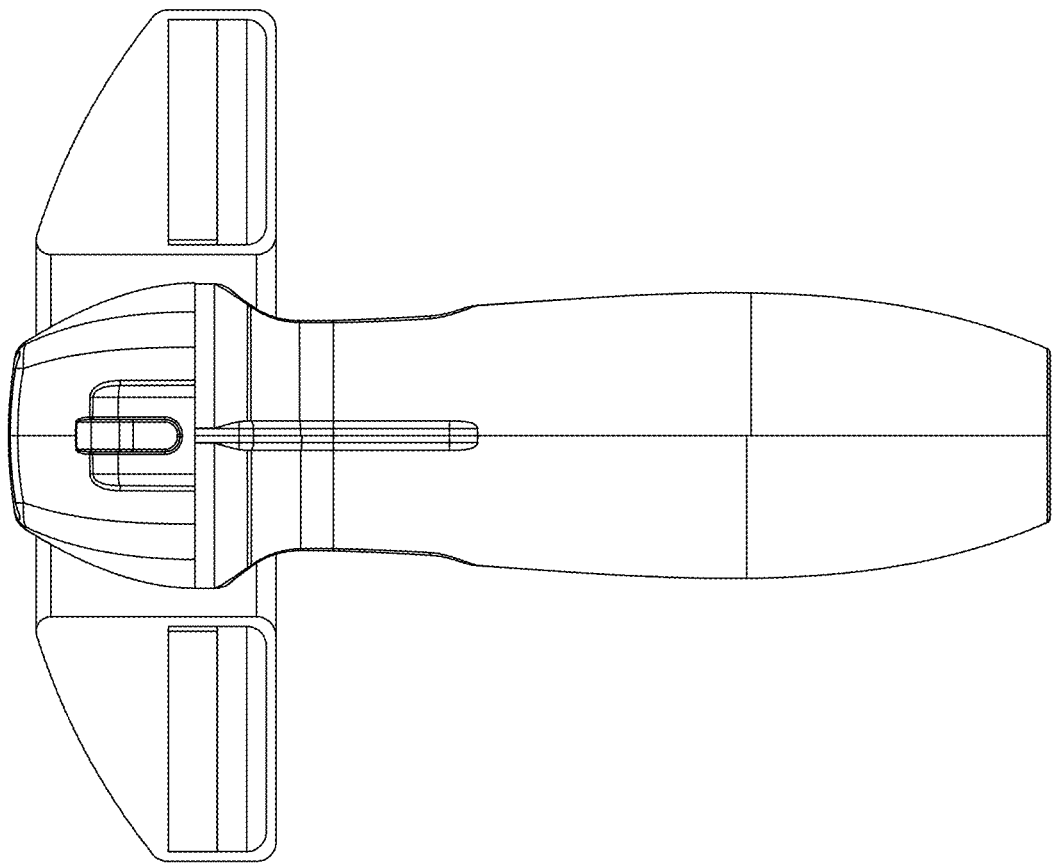

The plurality of elements of the therapy transducer can be any number compatible with the described methods. In one embodiment the segmented transducer having a plurality of elements has a number of elements selected from the group consisting of two elements, four elements, six elements and eight elements. In other embodiments the plurality of elements is greater than eight elements. The greater the number of elements, the more finely the generated ultrasound intensity field can be tailored spatially. FIG. 8A is an illustration of an exemplary probe comprising a single imaging element situated at the center of four therapy elements. FIGS. 8B and 8C are illustrations of an exemplary probe comprising a single imaging element situated at the center of eight therapy elements, wherein FIG. 8B is a perspective view and FIG. 8C is a longitudinal cross-sectional view.

In a basic illustration of the method, the therapy transducers are fired in-phase, producing a focal beam for a certain duration (e.g., FIG. 1A), then fired out of phase (π- or 180-degree phase shift) for a certain duration (e.g., FIG. 1B), repeating this sequence at a certain pulse repetition frequency to achieve a weighting of phase pattern duty factors.

The two duty factors can be applied to "weight" the individual beam contributions to the time-averaged intensity profile (e.g., $I_{SPTA}$). Alternatively, the amplitudes of the two elements can be adjusted simultaneously with the phase to apply a weighting function.

Figure 3A:
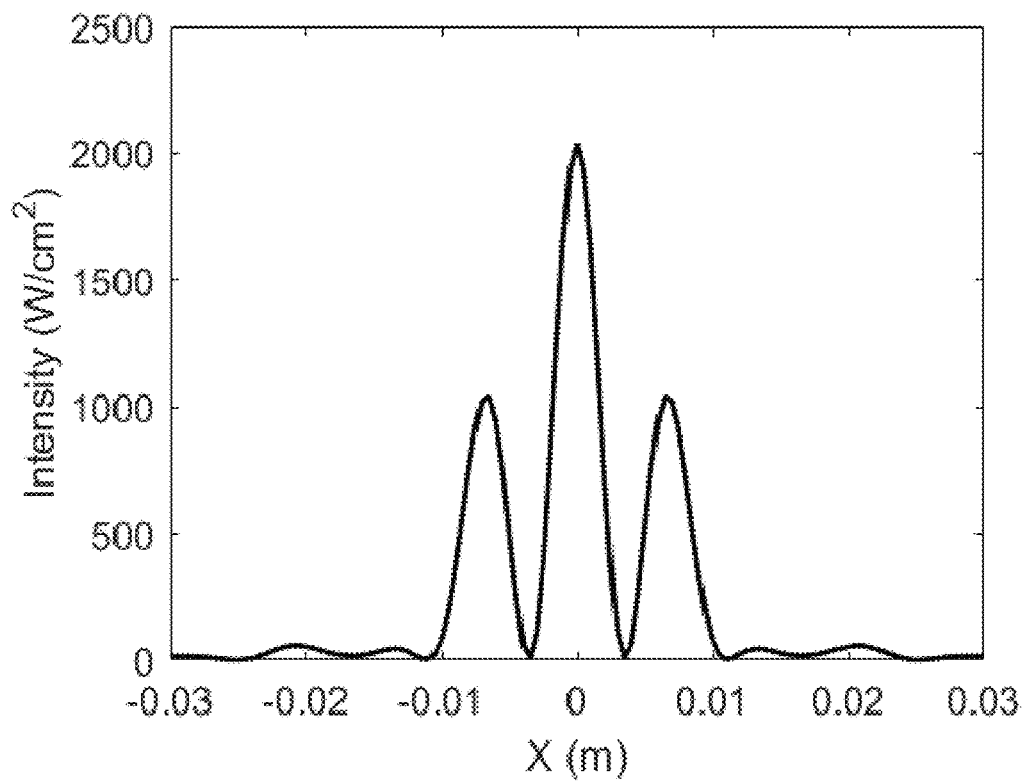
FIGS. 3A-3C. Beam plots of FIGS. 2A-2C, respectively, across the x-axis at peak intensity. Note the smooth time-average intensity profile despite the more spatially-varied individual profiles.
Figure 3B:
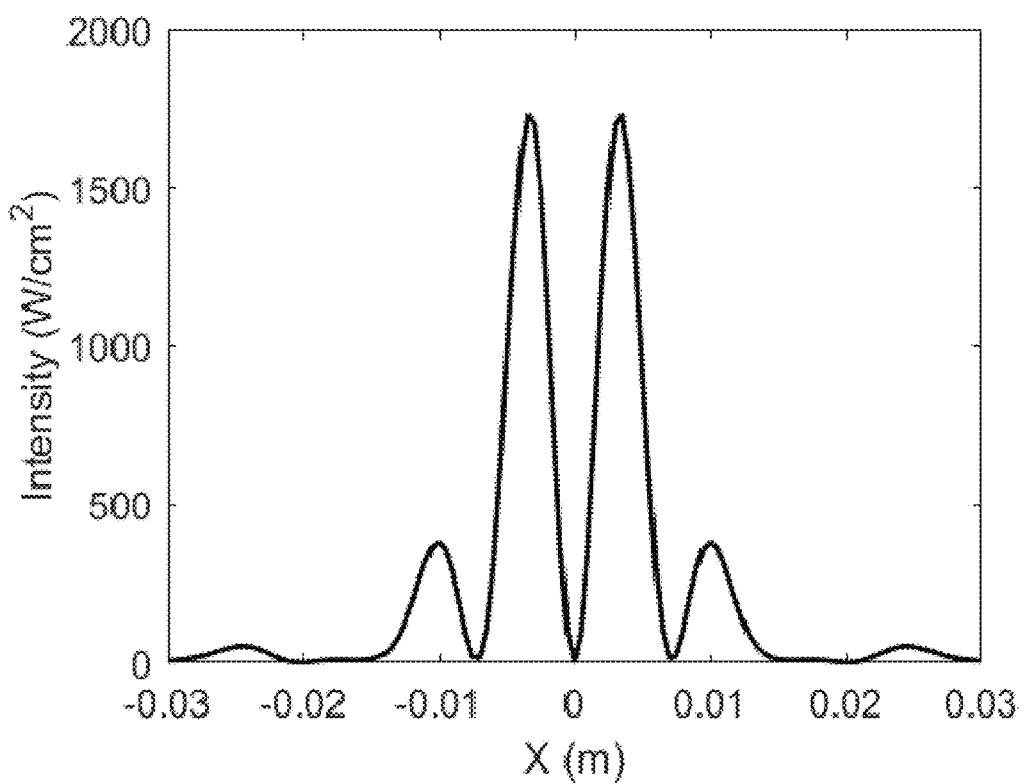
Figure 3C:
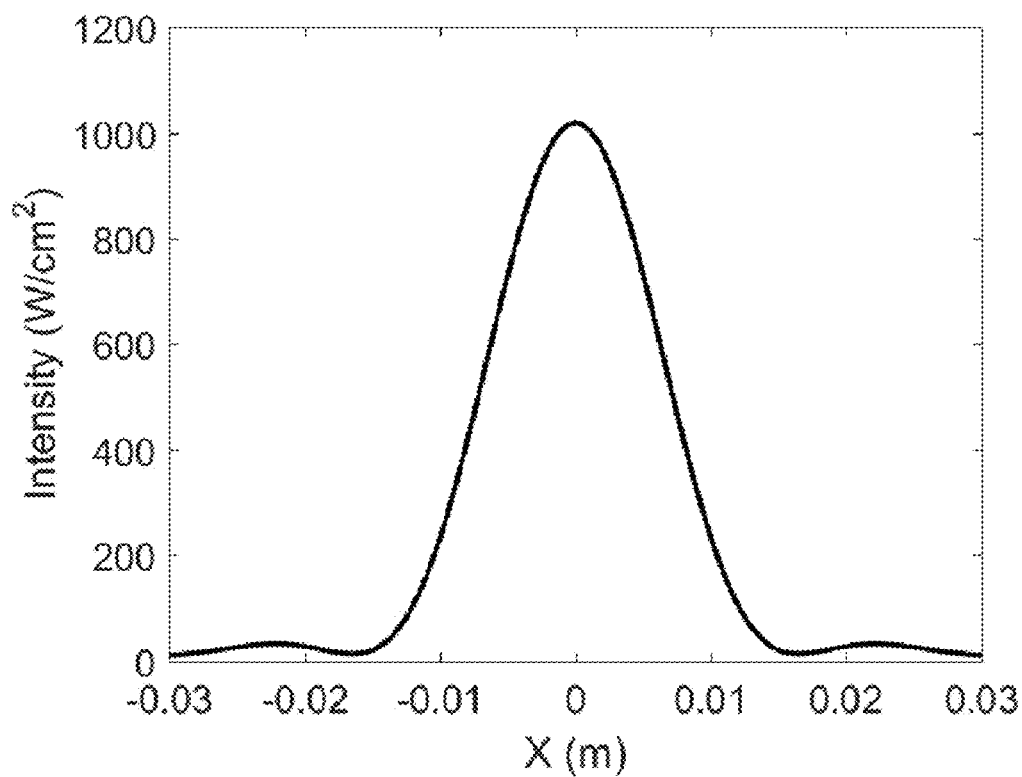

The two independent pressure fields are shown in FIGS. 1A and 1B, and the combined, time-average intensity fields are shown in FIGS. 2A-2C, assuming a 1:1 weighting of each pattern, which illustrates the summation (FIG. 2C) of the time-averaged intensity field distributions of the in-phase (FIG. 2A) and out-of-phase (FIG. 2B) fields from FIGS. 1A and 1B. FIGS. 3A-3C are beam plots of FIGS. 2A-2C, respectively, across the x-axis at peak intensity. Note the smooth time-average intensity profile despite the more spatially-varied individual profiles.

Similar time-averaged intensity profiles can be produced with other phase-shift sequences. For example, the two elements can be fired in quadrature with a phase shift of +π/2 (+90 degrees) for a certain duration and with a phase shift of −π/2 (−90 degrees) for a certain duration. Another example would be to vary the phase shift continuously by operating the two elements at just slightly different frequencies such that the phase shift between elements varies continuously over the range of 0 to 2*π (0 to 360 degrees). This continuously varying phase shift between elements might be more practically implemented by sequentially changing the phase shift between elements sequentially through a series of more than two steps, operating the two elements for a certain duration at each step. The continuous phase variation (or pseudo-continuous, step-wise phase variation) can provide additional therapeutic advantage by producing a time-averaged transverse radiation force perpendicular to the acoustic axis (left or right along the x-axis of FIG. 1A or 1B) together with the primary propulsion force (in the z-direction), thus displacing an object in a lateral direction.

In one embodiment, the plurality of phasing profiles applied to the plurality of elements comprises a plurality of amplitudes. In one embodiment, the focal pressure amplitude is less than or equal to 3 MPa (300 W/cm$^2$ intensity) for ultrasound pushing. In one embodiment, the focal pressure amplitude is about 3-10 MPa for BWL. In one embodiment, the focal pressure amplitude is about 6-8 MPa for BWL.

In a further embodiment the pulse lengths remain constant while the amplitudes vary.

In one embodiment the plurality of phasing profiles applied to the plurality of elements comprises a plurality of pulse lengths. In one embodiment, related to BWL, the pulse length is about 10-100 cycles. In one embodiment related to ultrasound pushing, the pulse length is 100 cycles or greater. In one embodiment related to ultrasound pushing, the pulse length is 1000 cycles or greater. In a further embodiment the pulse lengths change while the amplitudes remain the constant.

In one embodiment the pulse lengths and the amplitudes vary. In such an embodiment nonlinear effects from high amplitude could be mitigated by weighting pulse length for certain beams.

The frequency of the ultrasound of the plurality of phasing profiles can be the same or different between phasing profiles. In one embodiment, the frequency of the plurality of phasing profiles is 100-500 kHz. In a further embodiment, the frequency of the plurality of phasing profiles is 100-1000 kHz. In yet a further embodiment, the frequency of the plurality of phasing profiles is 200-600 kHz. In yet a further embodiment, the frequency of the plurality of phasing profiles is less than 500 kHz.

The pulse repetition frequency (PRF) can be very high. In one embodiment the PRF is 100 Hz to 10 kHz. In a further embodiment the PRF is 100-1000 Hz.

The therapy region created by the ultrasound can be adjusted by the user and is typically selected by the object to be impinged with the ultrasound. In one embodiment the therapy region is 0.1-20 mm wide. In one embodiment the therapy region is 10-10 mm wide. Width of the therapy region can be further understood with reference to U.S. Patent Application Publication Number U.S. 2017/0245874, the disclosure of which is hereby incorporated by reference in its entirety.

In one embodiment, the time-averaged intensity profile is generated by activating a first element of the plurality of elements and a second element of the plurality of elements in phase for a first time duration, and subsequently activating the first element and the second element out of phase for a second time duration.

In one embodiment, the time-averaged intensity profile is generated based, at least in part, on adjusted amplitudes during the first time duration relative to adjusted amplitudes during the second time duration. This embodiment has presently been used to generate experimental data in BWL studies by adjusting the amplitude of the central beam (m=0) to provide the same peak pressure as the vortex (m=1). BWL is more concerned with spatial and temporal peaks than UP, which is mostly based on time-average and spatial-average intensity.

In one embodiment, the first time duration and the second time duration are of equal time durations. Conversely, in one embodiment, the first time duration and the second time duration are of unequal time durations.

In one embodiment, the method further includes a time delay between the first time duration and the second time duration. In one embodiment, to accommodate imaging, the delay is 100 microseconds to 50 milliseconds. In a further embodiment, the time delay is coordinated with an imaging ultrasound signal so as to image the object between the first time duration and the second time duration.

In one embodiment, the time-averaged intensity profile is generated based, at least in part, on the length of the first time duration relative to the length of the second time duration.

In one embodiment, the time-averaged intensity profile is generated based, at least in part, on adjusted amplitudes of either the first element or the second element relative to the other.

In one embodiment, the time-averaged intensity profile is generated based, at least in part, on generating vortex patterns in sequence to create a complementary series of patterns that collectively create a region of time-averaged intensity.

Figure 4A:
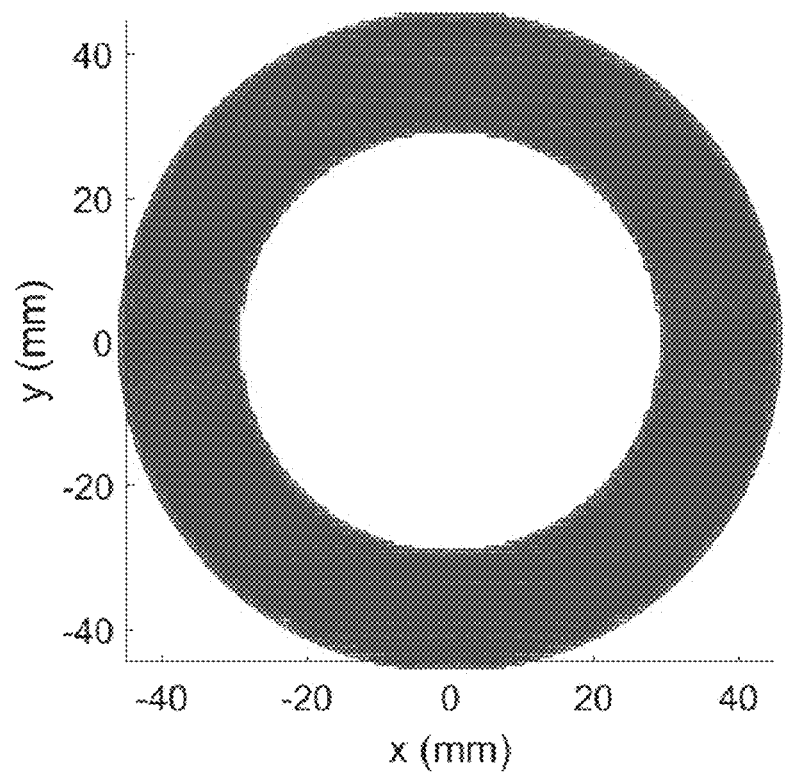
FIGS. 4A-4C.
Figure 4B:
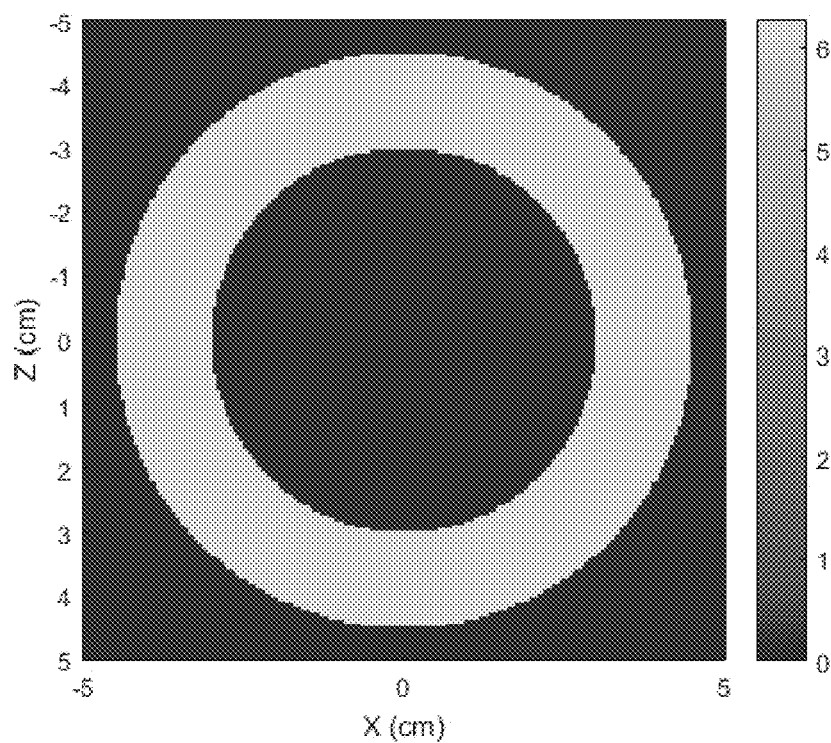
Figure 4C:
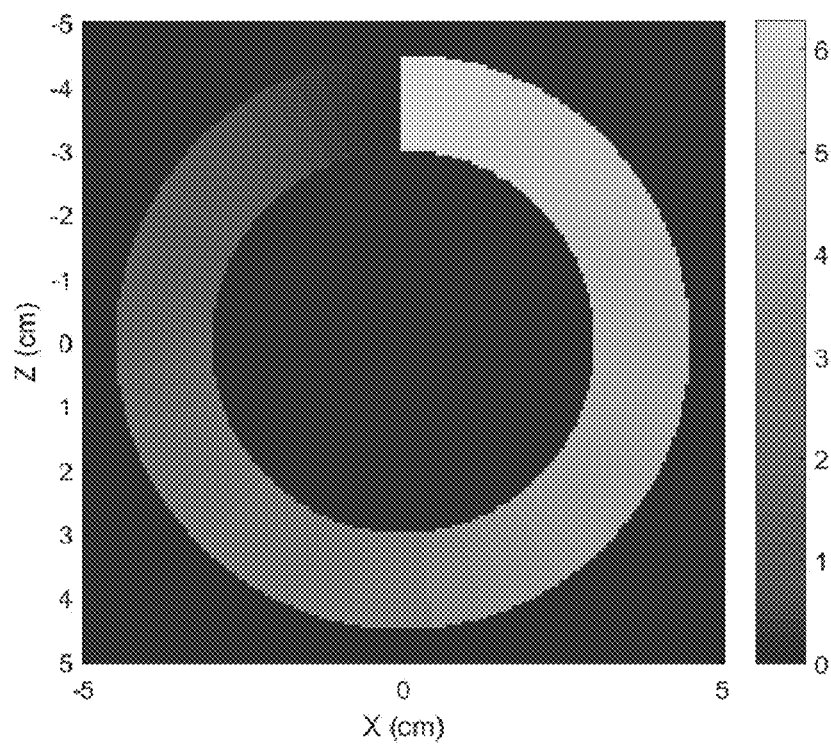

More complex situations can be realized using a polar configuration such as a sector array. In a representative embodiment a large hole is placed in the middle of a focused transducer to house the imager, leaving an annulus to perform the therapy, as illustrated in FIGS. 4A-4C. This hole decreases the beam-width of the focus, which is problematic for ultrasonic propulsion. In this case, vortex patterns can be made in sequence to create a complementary series of patterns that will create a large region of equal time-average intensity, and therefore pressure.

Vortex patterns are generated by phasing elements arranged in a sectoral pattern according to their circumferential position. For a transducer of circular or annular aperture composed of N sectors, the relative phase between elements to achieve a vortex pattern can be written as $\phi_n = m\theta_n$, where $\phi$ is the excitation phase, $\theta$ is the circumferential angle of the sector position of element n, and m is an integer $0 \leq m \leq N/2$. For a circular sector array with evenly spaced elements, this can alternatively be written as $$\phi_n = 2\pi \frac{mn}{N}.$$

This value m dictates the size of the vortex, and is commonly referred to as the 'topological charge' of the vortex beam.

FIG. 4A is a projection of an exemplary transducer layout and phasing to achieve vortex beams. A uniform phase distribution (m=0) is applied to the elements of an annular transducer, producing a focused beam in FIG. 4B. A transducer profile with an m=1 vortex phasing is shown in FIG. 4C. In practice, the transducer phasing may be separated into sectors that are driven with phase shifts corresponding to their circumferential position. The color scales on FIGS. 4B and 4C are angular phase—with FIG. 4B illustrating constant angular phase.

Figure 5A:
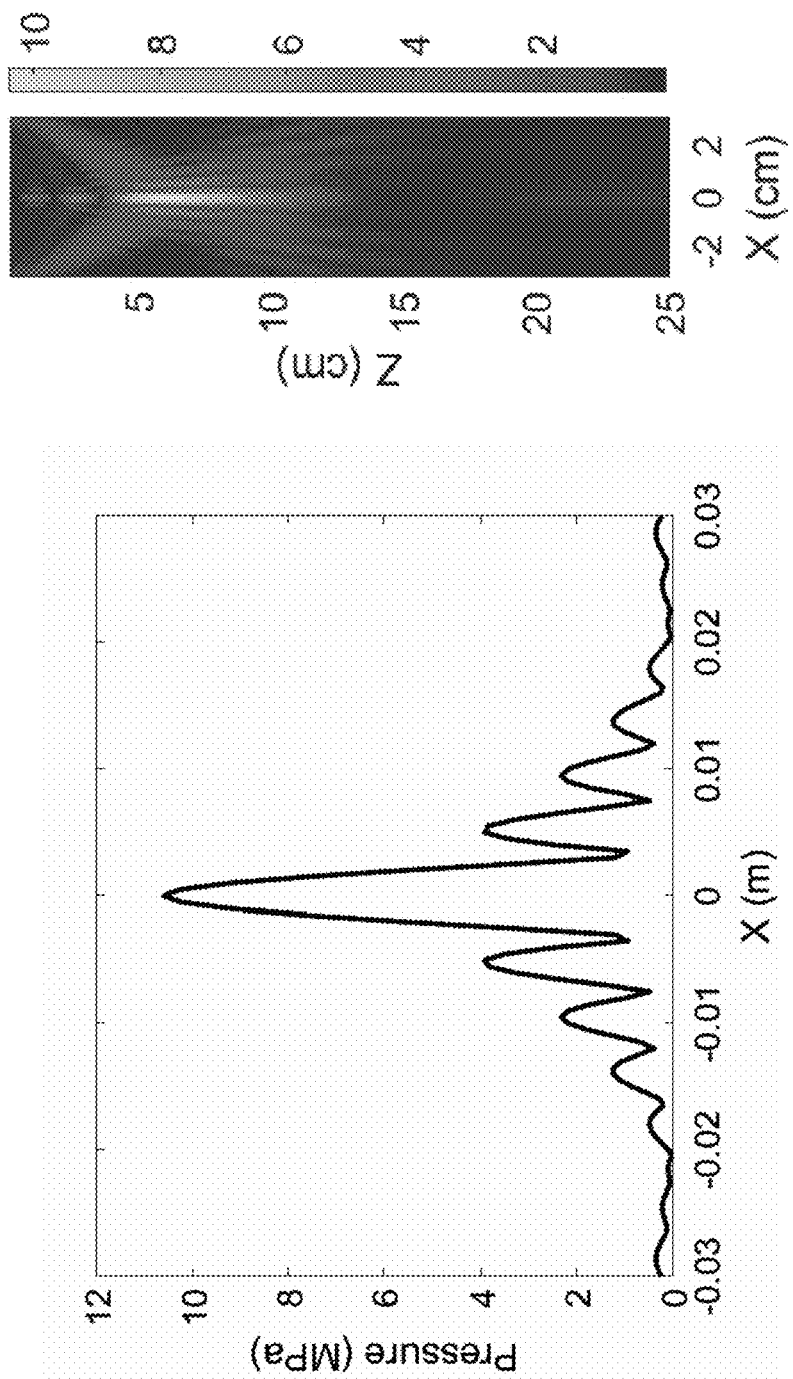

FIGS. 5A-5C are graphs produced from a sector array, illustrating pressure distribution along the x-axis (left) and x-z distribution of the field (right) produced for sector vortex phasing patterns with topological charge m=0, 1, 2 in FIGS. 5A, 5B, and 5C respectively. These show variation in the individual beam patterns generated.

Figure 6A:
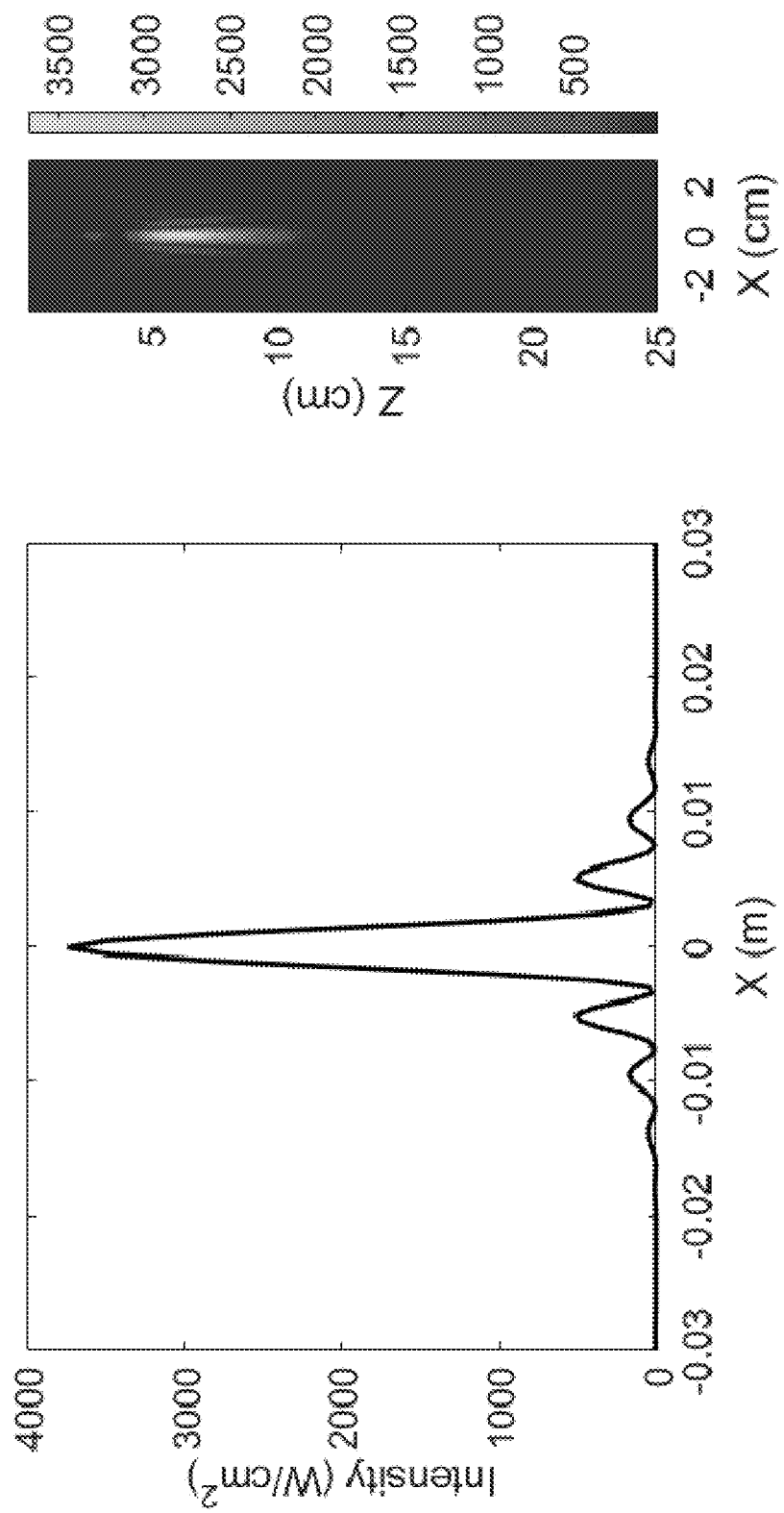
FIGS. 6A-6C. Effective x-axis beam intensity plots (left) and field-intensity plots (right) for the transducer in FIGS. 4A-4C, with corresponding topological charge pressure output weightings for m=0, 1, 2 of [1 0 0] (FIG. 6A), [1 1.5 0] (FIG. 6B), and [1 1.5 1.4] (FIG. 6C).
Figure 6B:
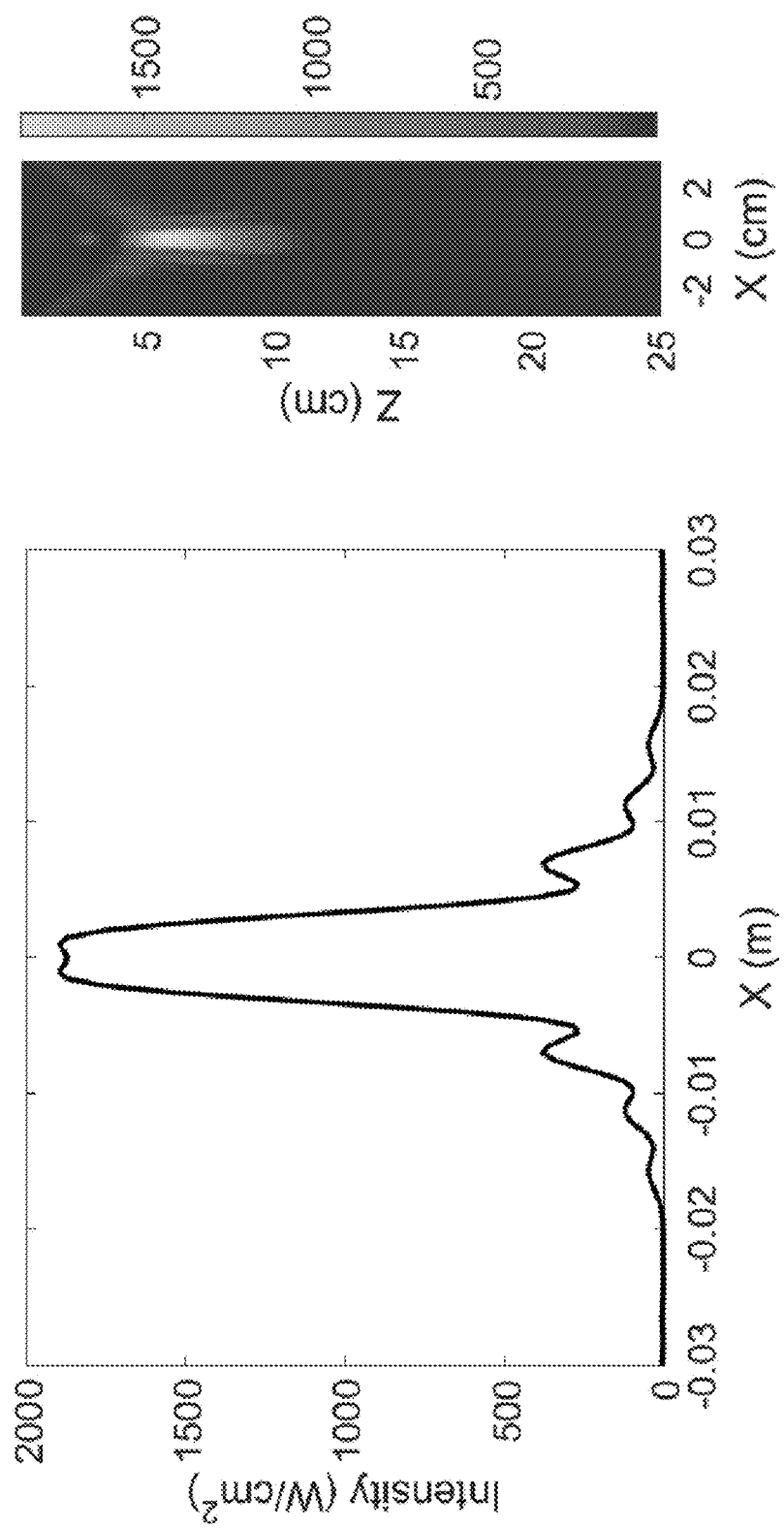
Figure 6C:
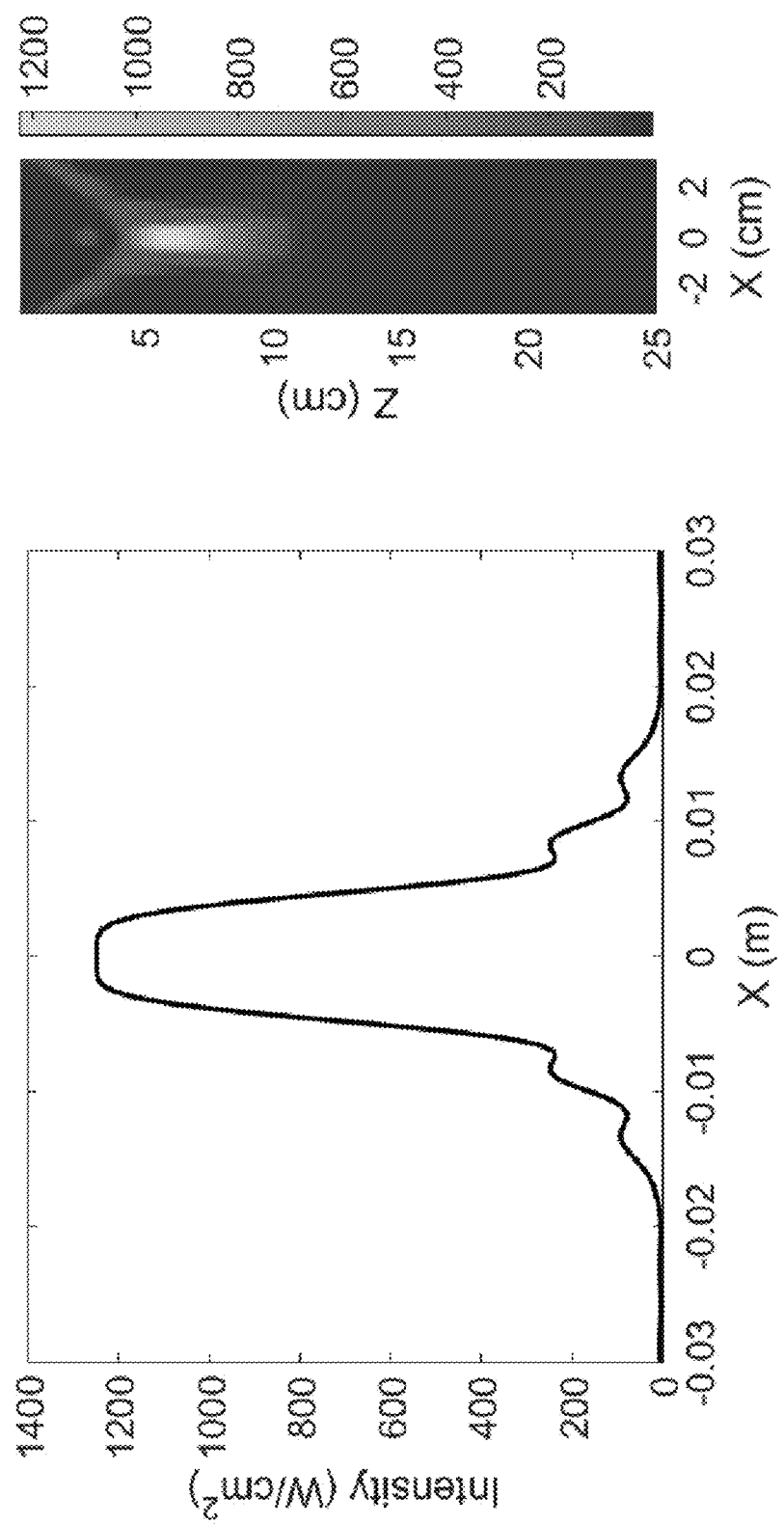

FIGS. 6A-6C. Illustrates effective x-axis beam intensity plots (left) and field-intensity plots (right) for the transducer in FIG. 4A, with corresponding topological charge pressure output weightings for m=0, 1, 2 of [1 0 0] (FIG. 6A), [1 1.5 0] (FIG. 6B), and [1 1.5 1.4] (FIG. 6C), showing −3 dB beam widths of 3.2 mm, 6 mm, and 10 mm, respectively (−6 dB or half-pressure are 4.2 mm, 8 mm, and 12 mm respectively). These FIGURES capture the uniformity that is not achieved in a beam in FIG. 5A-5C.

Use with Burst Wave Lithotripsy

In one embodiment, applying the ultrasound energy to the object comprises applying burst wave lithotripsy sufficient to break the object into at least two pieces. Burst wave lithotripsy (BWL) is a technique for breaking kidney stones. This technology uses a burst of sinusoidal focused ultrasound waves with amplitude lower than shock waves to fragment stones, and has several unique features that make it attractive for treating stones. BWL has been shown to fragment most types of stones in vitro, and has the capability to control the size of fragments generated by varying the ultrasound frequency. Studies indicate that fragmentation can occur at focal pressure amplitudes down to 3 MPa, low enough to avoid injury to the kidney. BWL applies broadly focused bursts of ultrasound, rather than shock waves, to break stones by exciting natural acoustic resonances in the stone and/or by promoting cavitation damage at nucleation sites associated with the stone itself.

Experimental data suggests that the larger the stone, the broader the BWL beam must be in order to effectively break the stone apart. In some embodiments of BWL, the same concept and geometry as in UP is used wherein the therapeutic elements are placed in an annular ring around the ultrasound imaging probe at the center. To broaden the BWL therapeutic beam, the same phase modulation concept can be used where the different BWL elements are excited out of phase or at slightly different frequencies. In some cases, we have observed that it is helpful to mechanically scan the beam around the stone, rather than just aiming at the middle of the stone and leaving it there. This same effect can be achieved by using phase modulation to electronically steer the beam.

One obstacle to rapid and efficacious BWL treatment is that the high peak pressures associated with the focused ultrasound beam can give rise to cavitation in the fluid medium proximal to the stone to create a cavitation "bubble cloud," which then shields the stone from subsequent ultrasound pulses, while the bubble cloud is further reinforced. This problem has been identified in association with shock wave lithotripsy (SWL) operating at extremely high peak acoustic pressures of approximately 100 MPa. The traditional solution to this problem is to limit the pulse repetition frequency (PRF) to give a nascent bubble cloud sufficient time to dissipate between successive therapy pulses. For the high pressures associated with SWL, the PRF may be limited to a maximum in the range of 0.5 Hz to 2 Hz, depending on the particular acoustic parameters of the SWL transducer. For the lower peak pressures associated with BWL, the maximum PRF to avoid the difficulties associated with bubble cloud formation may be in the range of 5 Hz to 200 Hz, again depending on the specific acoustic parameters associated with the treatment (e.g., beam dimensions and peak acoustic pressure).

In the absence of bubble cloud issues, a higher PRF translates to more rapid disintegration of the stone, so it is generally desired to maintain the highest possible PRF within the constraint of limiting bubble cloud formation and persistence. The disclosed method to allow maintenance of a high PRF while limiting bubble cloud persistence is to rapidly scan a narrow ultrasound beam such that sequential acoustic pulses do not precisely overlap one another. This keeps the effective PRF at a particular location below the threshold for bubble cloud persistence while maintaining the total PRF over the scanned area at a high rate. It may be difficult to achieve the required rapid scanning by mechanical means, but rapid scanning is easily achieved by adjusting the phase shifts among transducer elements between successive pulses, as disclosed herein. For example, if the two beams illustrated in FIGS. 3A and 3B are alternated, the PRF for a particular spatial peak pressure would be one-half the overall PRF, and the treatment might be completed in one-half the time otherwise required. For a more complex beam pattern and with more elements comprising the transducer array, the overall PRF might be increased by a factor of 4 times, to complete the treatment in one-quarter the time or less.

Breaking and/or Moving Objects Using the Ultrasound Energy

The ultrasound energy applied to the object can be used to break (as discussed above specifically with regard to BWL) and/or move the object, depending on the preferences of the operator. The character of the beam can be modified so as to focus the ultrasound energy on a specific object or even a specific portion of a larger object. Accordingly, in one embodiment, the plurality of phasing profiles are used to focus the ultrasound energy on a specific portion of the object.

In one embodiment, applying the ultrasound energy to the object comprises applying an ultrasound radiation force sufficient to move the object relative to the patient. In such an embodiment, the ultrasound energy, and particularly the time-averaged intensity, is sufficient to move the object within the patient. As an example, this may include moving a kidney stone within the patient so as to facilitate passing of the stone by the patient. As noted elsewhere herein, the size, intensity, and shape of the ultrasound beam can be tailored to deliver precisely shaped and sized ultrasound energy.

In one embodiment, applying the ultrasound energy to the object breaks the object into at least two pieces. If the amount of the ultrasound energy is sufficient an object will break into at least two pieces. Increasing the ultrasound energy can be effected by increasing intensity, pulse duration, PRF, and other ultrasound characteristics.

Figure 10A:
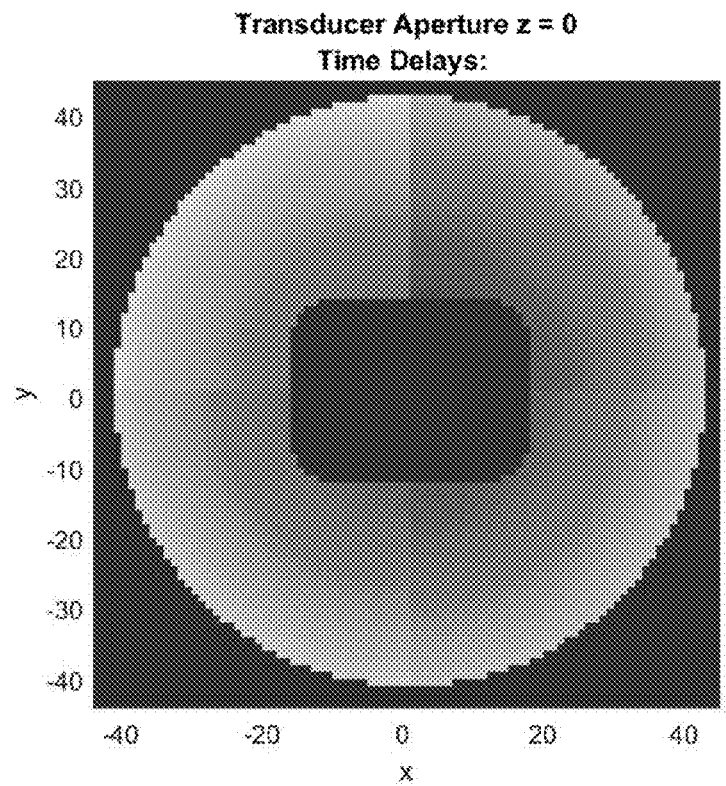
FIGS. 10A-10C are simulated vortex beam profile of the probe of FIGS. 9A-9C, including a null or no-pressure zone in the middle.

In a further embodiment, the method additionally includes applying ultrasound energy that produces an ultrasound radiation force sufficient to move the at least two pieces of the object relative to the patient. In such an embodiment, the method is used to first break the object (e.g., stone) and then move the pieces of the broken object (e.g., stone fragments). This is useful to move fragments so as to assist the patient's body in passing them, or to collect fragments in a concentrated location such that fragments do not escape a defined area so as to irritate the patient. In the latter case, generating an ultrasound beam with pressure minimum at the center, such as in FIGS. 10-12, will enable collection and capture of fragments at the center of the beam.

Imaging

Imaging can be an important component of an effective therapy using the disclosed methods on a patient. By integrating imaging with the therapy ultrasound, a technician can better understand the effects of the therapy ultrasound on the object impacted by the therapy ultrasound. Accordingly, in one embodiment, the method further includes imaging the object using imaging ultrasound signals. In one embodiment, the imaging ultrasound signals are provided by an imaging transducer.

In certain embodiments, during operation, the therapy probes emit a therapy exposure comprising a plurality of ultrasonic therapy pules over a therapy exposure time (refer to FIG. 11 for a visual illustration of the therapy exposure signal). If imaging is utilized, the therapy probe and imaging probe are coordinated such that their signals do not overlap yet images are acquired frequently enough (e.g., at least one frame per second, fps). By acquiring images of the therapy region during a therapy exposure, the operator can see the movement of stones in real time and adjust aim and/or focus as needed to accomplish the treatment (e.g., move the stones towards expulsion from the kidney or other region).

In one embodiment, the imaging transducer is integrated into a housing with the segmented transducer. In one embodiment, the imaging transducer is removably couplable to the housing. Imaging probes are illustrated in, for example, FIGS. 7A-8C, as described elsewhere herein.

Ultrasound System and Computer-Readable Media for Performing the Methods

In another aspect a system for applying an ultrasound force to an object disposed in a patient is provided. In one embodiment, the system includes:

a multi-element transducer having a first element and a second element, wherein the multi-element transducer is configured and arranged to perform any of the methods disclosed herein. Any ultrasound system capable of effecting the method steps disclosed herein is compatible with the provided system aspect. An exemplary system is illustrated in FIG. 14 of US 2017/0245874, incorporated herein by reference; such a system includes at least a segmented ultrasound transducer (therapy probe) to provide the ultrasound energy via the plurality of phasing profiles as described herein. The therapy probe is controlled by a control unit that includes a CPU or other control electronic interface capable of receiving input from a user allowing them to modify the character of the ultrasound energy (e.g., modify the phasing profiles, adjust focus, adjust intensity, etc.). Separate or co-housed with the control unit is an amplifier configured to power the therapy probe and provide the desired power signals so as to produce the desired ultrasound energy and implement the phasing profiles. In certain embodiments, an imaging probe is also utilized, as disclosed herein.

In yet another aspect, provided is a non-transitory computer-readable medium having computer executable instructions stored thereon that, if executed by one or more processors of a computing device, causes the computing device to perform any of the methods disclosed herein. As an example, the disclosed media in certain embodiments allows a user to provide control instructions, via the control unit, to the therapy probe, including defining the character of the ultrasound energy as disclosed herein. In a further embodiment, the media is configured to provide cooperation between the therapy probe and an imaging probe so as to allow concurrent use of the two probes, thus allowing a user to apply therapy ultrasound and visually track progress of the therapy using imaging ultrasound. The media, in other embodiments, allows a user to select between modes of operation, such as selecting "pushing" or "breaking" modes and adjusting the character of the therapy ultrasound accordingly.

Simulated Beam Profile of Four-Element Therapy Probe

The simulations of FIGS. 1A-6C were generated as follows. Simulations of the phasing were performed using the Rayleigh integral. Intensity was calculated from the complex pressure field using a plane wave approximation.

Figure 9A:
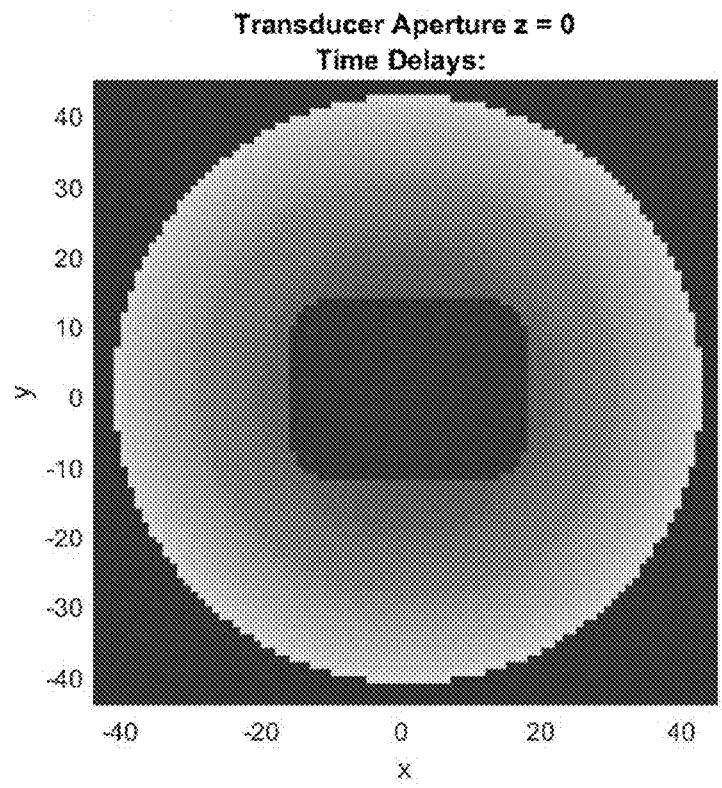
FIGS. 9A-9C are simulated beam profiles of a four element therapy probe (e.g., FIG. 8A) when there is a 90-degree phase shift between the elements. The hole in the middle is for the imaging probe.
Figure 9B:
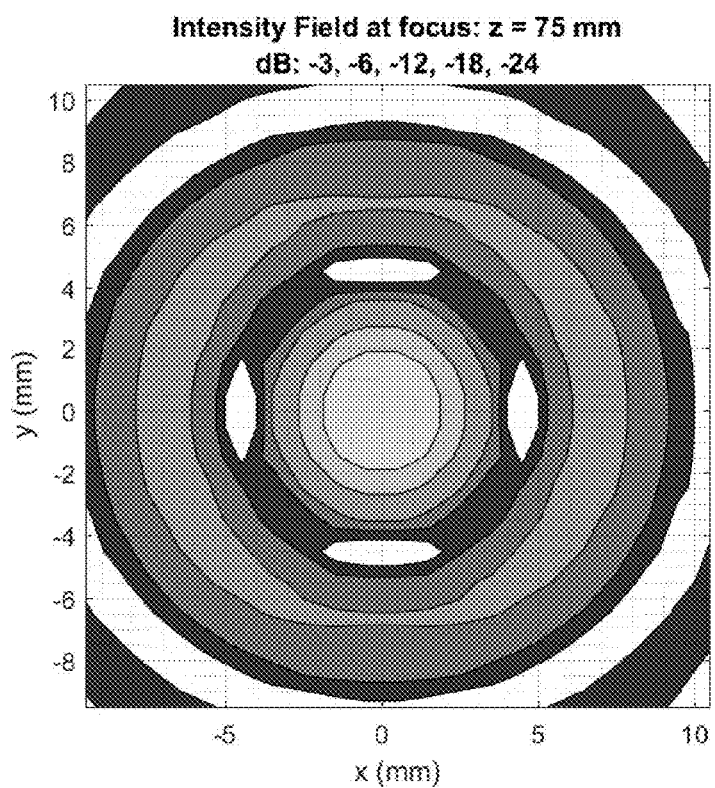
Figure 9C:
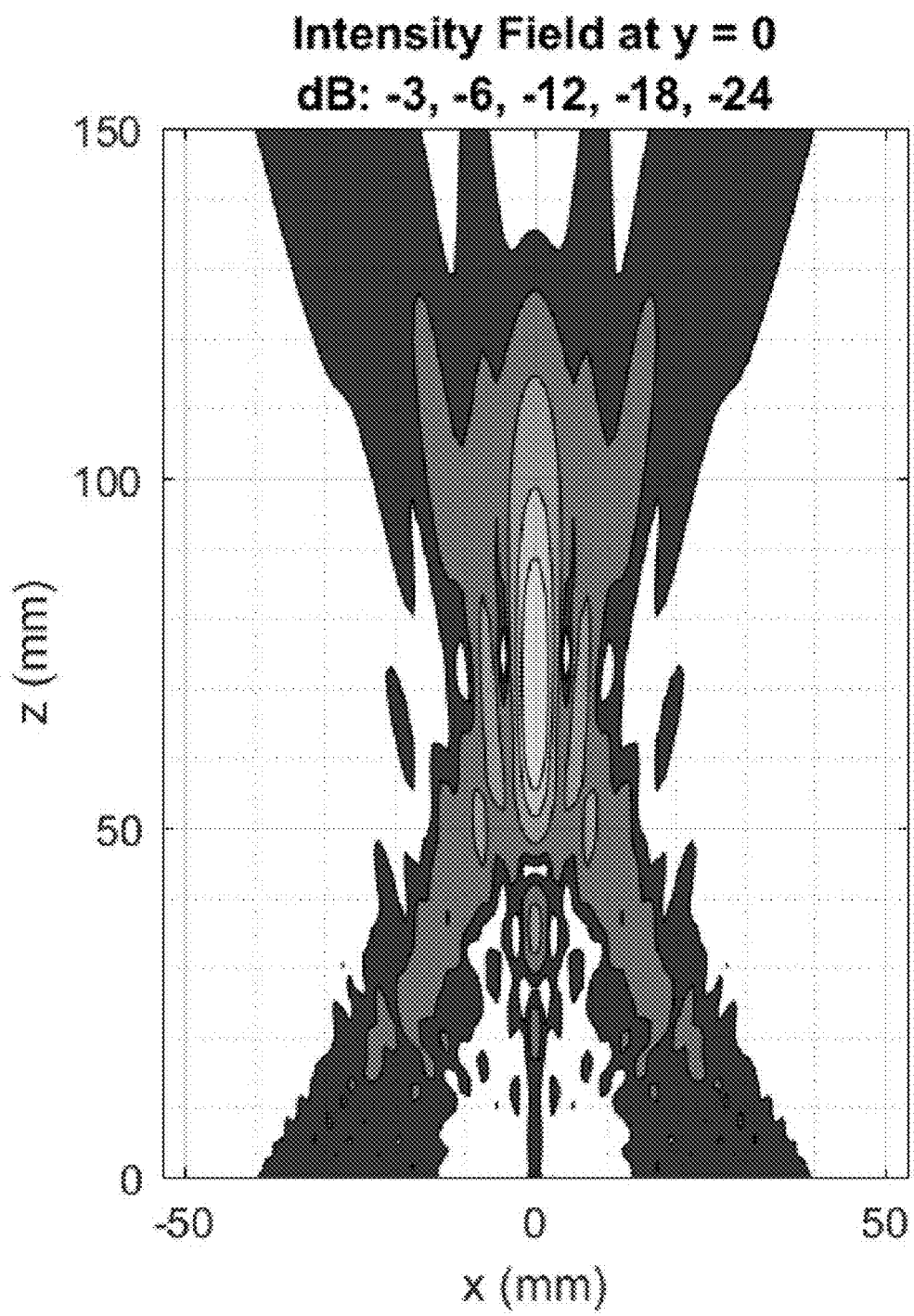

Beam characteristics for the four-element probe illustrated in FIG. 8A et al. were calculated using the FOCUS Ultrasound Simulator software from Michigan State University (see: http://www.egr.msu.edu/-fultras-web/). FIG. 9A shows the aperture of the probe, with the colors representing the time delay required for a spherical focus at a 75 mm focal depth. The hole in the middle is to accommodate the imaging probe. In this case, there is no extra phase shift introduced between elements, and the beam is centrally focused (topological charge, m=0). FIG. 9B shows a contour plot of the corresponding ultrasound beam pattern in the xz-plane, illustrating the convergence of ultrasound at the nominal focus on the central axis of the beam at an exemplary depth of approximately 75 mm. FIG. 9C shows a contour plot of a cross-section of the ultrasound beam, taken at the nominal focal depth of 75 mm. The central peak has a 3 dB diameter of approximately 4 mm, and it is surrounded by the lower level sidelobes.

Figure 10B:
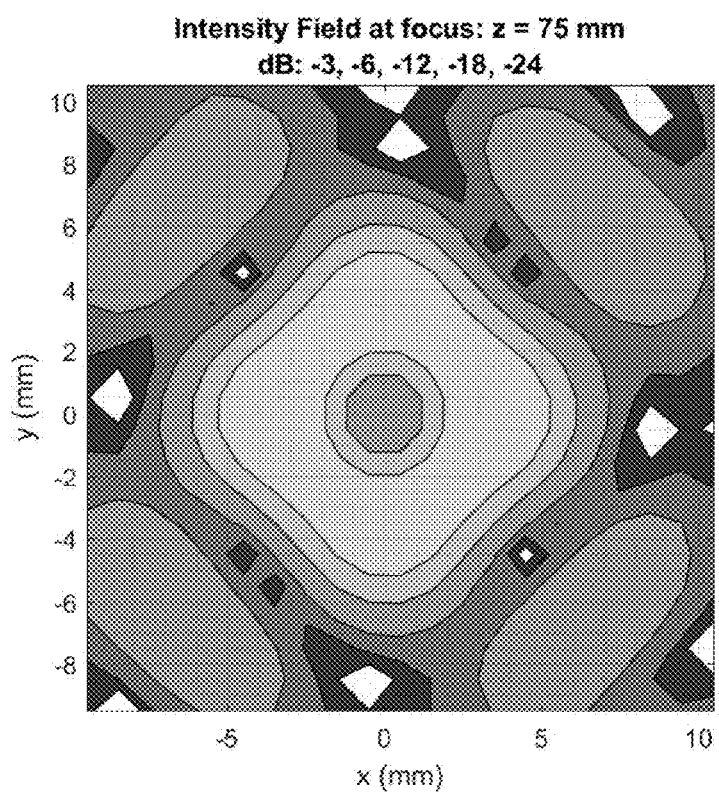
Figure 10C:
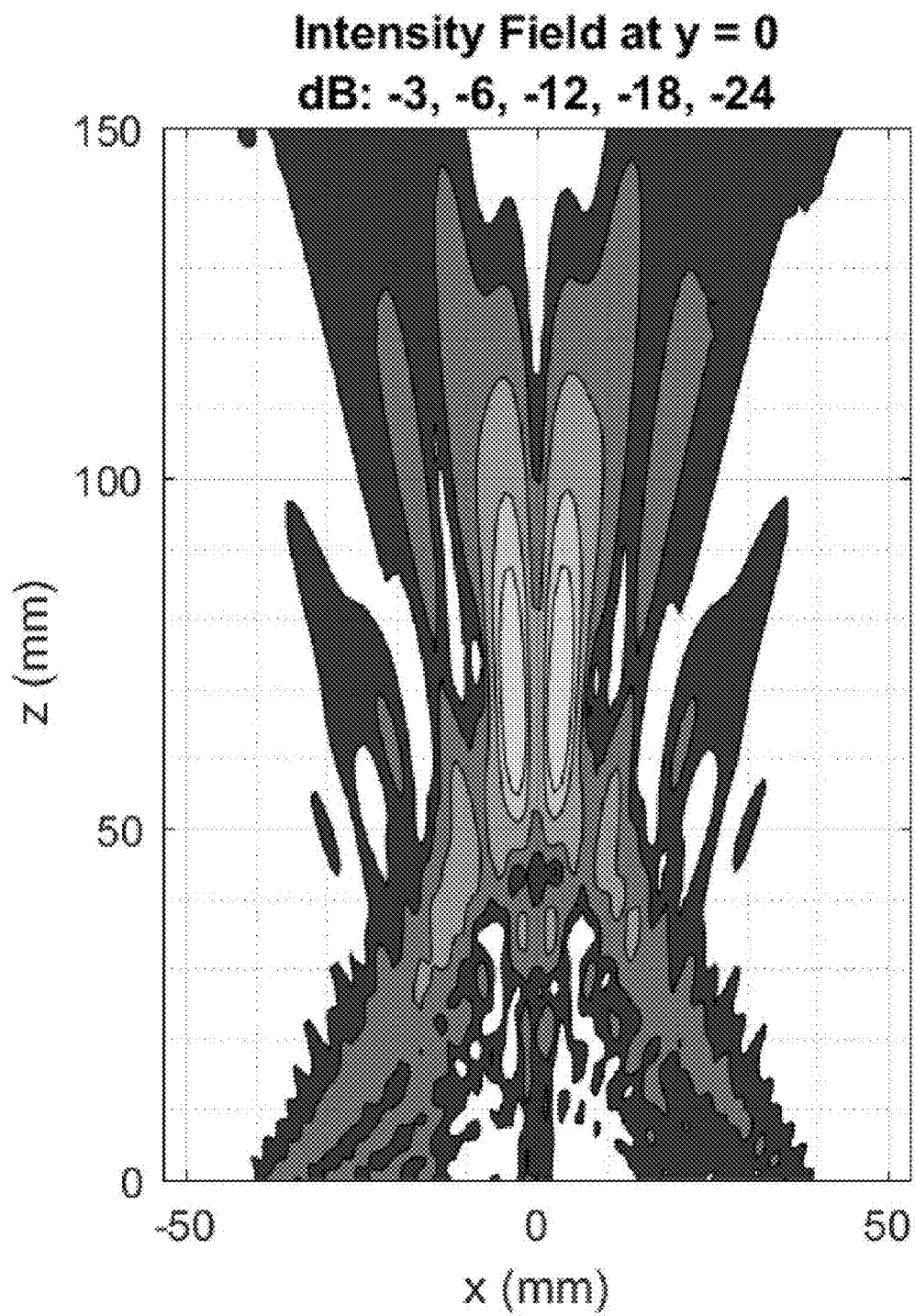

FIG. 10A again shows the aperture of the four-element probe illustrated in FIG. 8A, with the colors representing the time delay required for a spherical focus at a 75 mm focal depth. In this case, there is an additional phase shift introduced between elements ($\pi/2$ or 90° per element), to produce a vortex beam (topological charge, m=1). FIG. 10B shows a contour plot of the corresponding ultrasound beam pattern in the xz-plane, illustrating the convergence of beam at the nominal focal depth of 75 mm, but with a null on the central axis of the beam, and peaks on either side of the central axis. FIG. 10C shows a contour plot of a cross-section through the vortex ultrasound beam, taken at the nominal focal depth of 75 mm. The vortex beam forms a slightly diamond-shaped ring around the central axis of the beam, with a null in the middle, and with outer 3 dB contours in the range of 8 mm to 10 mm in width.

Combining the ultrasound beams of FIGS. 9C and 10C, by sequentially exciting the transducer elements with the appropriate phasing profiles will generate the effect of a composite beam that has the large outer dimensions of the vortex beam, but with the central null of the vortex filled by the contribution from the centrally focused beam. This approach provides an ultrasound beam having a time-averaged intensity profile that is generated over a larger area or more uniform than a comparative time-averaged intensity profile generated by the plurality of elements but without the plurality of phasing profiles.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for applying ultrasound energy to an object disposed in a patient, the method comprising applying ultrasound energy within a treatment comprising a plurality of therapy exposures, wherein the ultrasound energy is applied to the object using a segmented transducer having a plurality of elements excited by a plurality of phasing profiles;
   wherein, during a single therapy exposure comprising a series of ultrasound pulses over an exposure time, the plurality of phasing profiles is applied to the plurality of elements to generate a plurality of intensity profiles; and
   wherein, during the single therapy exposure, the plurality of phasing profiles exciting the plurality of elements collectively generates an ultrasound beam having a time-averaged intensity profile that is generated over a larger area or more uniform than a comparative time-averaged intensity profile generated by the plurality of elements but without the plurality of phasing profiles.

2. The method of claim 1, wherein the time-averaged intensity profile is generated by activating a first element of the plurality of elements and a second element of the plurality of elements in phase for a first time duration during the single therapy exposure, and subsequently activating the first element and the second element out of phase for a second time duration during the single therapy exposure.

3. The method of claim 2, wherein the first time duration and the second time duration are of equal time durations.

4. The method of claim 2, wherein the first time duration and the second time duration are of unequal time durations.

5. The method of claim 2, further comprising a time delay between the first time duration and the second time duration.

6. The method of claim 5, wherein the time delay is coordinated with an imaging ultrasound signal so as to image the object between the first time duration and the second time duration.

7. The method of claim 2, wherein the time-averaged intensity profile is generated based, at least in part, on the length of the first time duration relative to the length of the second time duration.

8. The method of claim 2, wherein the time-averaged intensity profile is generated based, at least in part, on adjusted amplitudes of either the first element or the second element relative to the other.

9. The method of claim 1, wherein the time-averaged intensity profile is generated based, at least in part, on generating vortex patterns in sequence to create a complementary series of patterns that collectively create a region of time-averaged intensity during the single therapy exposure.

10. The method of claim 1, wherein the plurality of phasing profiles are used to focus the ultrasound energy on a specific portion of the object during the single therapy exposure.

11. The method of claim 1, wherein applying the ultrasound energy to the object comprises applying an ultrasound radiation force sufficient to move the object relative to the patient.

12. The method of claim 1, wherein applying the ultrasound energy to the object breaks the object into at least two pieces.

13. The method of claim 12, wherein applying the ultrasound energy to the object comprises applying burst wave lithotripsy sufficient to break the object into the at least two pieces.

14. The method of claim 12, further comprising applying the ultrasound energy that produces an ultrasound radiation force sufficient to move the at least two pieces of the object relative to the patient.

15. The method of claim 1, further comprising imaging the object using imaging ultrasound signals.

16. The method of claim 15, wherein the imaging ultrasound signals are provided by an imaging transducer.

17. The method of claim 16, wherein the imaging transducer is integrated into a housing with the segmented transducer.

18. The method of claim 17, wherein the imaging ultrasound signals and the ultrasound energy are coordinated such that they do not temporally overlap.

19. The method of claim 1, wherein the segmented transducer having a plurality of elements has a number of elements selected from the group consisting of two elements, four elements, six elements and eight elements.

20. The method of claim 1, wherein the object is selected from the group consisting of a kidney stone, fragments, blood clots, bullets, mucous, cystic fibrosis mucous, flowing blood, impacted stool in constipation, rectal, urethral and bladder foreign bodies, ureteral stones, bladder stones, airway foreign bodies, nasal congestion, a sinus obstruction, impacted cerumen (ear wax), tissue flaps, floating objects in the eye, dust located in the gall bladder, the salivary tract, the biliary tract, and any other anatomical location of a human or other mammal.

* * * * *